US011883644B2

United States Patent
Nunez et al.

(10) Patent No.: US 11,883,644 B2
(45) Date of Patent: Jan. 30, 2024

(54) APPARATUS FOR CREATING RESONANT STANDING WAVES IN BIOLOGICAL TISSUE

(71) Applicant: INNOVARIUS LTD., London (GB)

(72) Inventors: Albert Nunez, Orlando, FL (US); Eric Miller, Orlando, FL (US); Gary Minker, Orlando, FL (US); Alex Nunez, Orlando, FL (US)

(73) Assignee: INNOVARIUS CORP., Maitland, FL (US)

(*) Notice: Subject to any disclaimer, the term of this patent is extended or adjusted under 35 U.S.C. 154(b) by 0 days.

(21) Appl. No.: 16/955,868

(22) PCT Filed: Dec. 19, 2018

(86) PCT No.: PCT/EP2018/085833
§ 371 (c)(1),
(2) Date: Jun. 19, 2020

(87) PCT Pub. No.: WO2019/121905
PCT Pub. Date: Jun. 27, 2019

(65) Prior Publication Data
US 2020/0316367 A1    Oct. 8, 2020

Related U.S. Application Data

(60) Provisional application No. 62/607,597, filed on Dec. 19, 2017.

(51) Int. Cl.
*A61N 1/04*    (2006.01)
*A61N 1/06*    (2006.01)
(Continued)

(52) U.S. Cl.
CPC ......... *A61N 1/0468* (2013.01); *A61N 1/0464* (2013.01); *A61N 1/06* (2013.01);
(Continued)

(58) Field of Classification Search
CPC ...... A61N 1/0464; A61N 1/0468; A61N 1/06; A61N 1/36021; A61N 1/36025; A61N 1/36034; A61N 1/403
(Continued)

(56) References Cited

U.S. PATENT DOCUMENTS

| 4,719,919 A | 1/1988 | Marchosky et al. |
| 5,190,037 A | 3/1993 | Di Mino et al. |

(Continued)

FOREIGN PATENT DOCUMENTS

| CN | 1657116 A | 8/2005 |
| EP | 2 703 042 A | 3/2014 |

(Continued)

OTHER PUBLICATIONS

International Search Report and Written Opinion for corresponding Patent Application No. PCT/EP2018/085833 dated Mar. 21, 2019.

*Primary Examiner* — Carl H Layno
*Assistant Examiner* — Jane C Kalinock
(74) *Attorney, Agent, or Firm* — Renner, Otto, Boisselle & Sklar, LLP

(57) ABSTRACT

An apparatus for creating resonant standing waves in biological tissue, in particular in the treatment of medical conditions, comprising at least one applicator for application to biological tissue and a drive unit for driving the at least one applicator simultaneously with AM modulated and FM modulated carrier signals in order to create resonant standing waves in the tissue.

20 Claims, 21 Drawing Sheets

(51) Int. Cl.
*A61N 1/36* (2006.01)
*A61N 1/40* (2006.01)

(52) U.S. Cl.
CPC ..... *A61N 1/36021* (2013.01); *A61N 1/36025* (2013.01); *A61N 1/36034* (2017.08); *A61N 1/403* (2013.01)

(58) Field of Classification Search
USPC .......................................................... 607/50
See application file for complete search history.

(56) References Cited

U.S. PATENT DOCUMENTS

| | | |
|---|---|---|
| 5,694,936 A | 12/1997 | Fujimoto et al. |
| 6,161,048 A | 12/2000 | Sluijter et al. |
| 6,246,912 B1 | 6/2001 | Sluijter et al. |
| 8,690,748 B1 | 4/2014 | Fu |
| 2004/0111084 A1 | 6/2004 | Brett |
| 2004/0230263 A1 | 11/2004 | Samulski |
| 2005/0015125 A1 | 1/2005 | Mioduski et al. |
| 2005/0251234 A1 | 11/2005 | Kanzius et al. |
| 2006/0161054 A1 | 7/2006 | Reuss et al. |
| 2006/0190063 A1 | 8/2006 | Kanzius |
| 2007/0123961 A1 | 5/2007 | Danek et al. |
| 2007/0299895 A1 | 12/2007 | Johnson et al. |
| 2008/0114428 A1 | 5/2008 | Trembly et al. |
| 2009/0036938 A1 | 2/2009 | Shipley et al. |
| 2011/0092884 A1 | 4/2011 | Kang |
| 2012/0065714 A1 | 3/2012 | Szasz et al. |
| 2013/0048880 A1* | 2/2013 | Einziger .................. H05B 6/72 250/492.1 |
| 2013/0245444 A1* | 9/2013 | Rybyanets ............... A61B 8/00 600/439 |
| 2013/0317576 A1 | 11/2013 | Rogers et al. |
| 2014/0065664 A1 | 3/2014 | Aknine et al. |
| 2014/0224021 A1 | 8/2014 | Edwards et al. |
| 2015/0217124 A1 | 8/2015 | Szasz et al. |
| 2016/0074668 A1* | 3/2016 | Nunez ................... A61N 5/025 607/101 |
| 2016/0339273 A1 | 11/2016 | Al Mayiah |

FOREIGN PATENT DOCUMENTS

| | | |
|---|---|---|
| EP | 3 231 478 A | 10/2017 |
| JP | S57/157164 A | 9/1982 |
| JP | 2007/536016 A | 12/2007 |
| JP | 2012/515604 A | 7/2012 |
| WO | 2011/138675 A2 | 11/2011 |
| WO | 2012/038891 A1 | 3/2012 |
| WO | 2016/040867 A1 | 3/2016 |
| WO | 2017/142948 A1 | 8/2017 |

* cited by examiner

APPARATUS FOR CREATING RESONANT STANDING WAVES IN BIOLOGICAL TISSUE

BACKGROUND OF THE INVENTION

The present invention relates to an apparatus for and a method of creating resonant standing waves in biological tissue, in particular in the treatment of medical conditions.

The present invention has application in acting to energize biological tissue to increase the potential energy of water in the tissue in vivo, which is postulated to separate charges of water into positive water ions outside of a negative EZ water layer that forms along hydrophilic membranes in a region of the tissue, and also in enhancing protein unfolding in the tissue.

In one aspect the present invention provides an apparatus for creating resonant standing waves in biological tissue, in particular in the treatment of medical conditions, comprising at least one applicator for application to biological tissue and a drive unit for driving the at least one applicator simultaneously with AM modulated and FM modulated carrier signals in order to create resonant standing waves in the tissue.

SUMMARY OF INVENTION

In one embodiment the apparatus comprises a single applicator.

In another embodiment the apparatus comprises a plurality of applicators.

In one embodiment the applicators are arranged in one or more arrays.

In one embodiment the least one applicator comprises a director layer which includes coupling slots, a Z-patch layer which includes a Z-patch and overlies the director layer, and a reflector layer which includes a patterned reflector for defining the polarity ratio.

In one embodiment the or each AM modulated carrier signal has a plurality of AM modulation frequencies of changing frequency, as an AM modulation composition set, applied thereto in succession for respective periods of time.

In one embodiment a plurality of FM modulated carrier signals are applied simultaneously to the at least one applicator.

In one embodiment the at least one applicator has three different FM modulated carrier signals applied thereto, as a triplet.

In one embodiment one or more of the FM modulated carrier signals have a plurality of FM modulation frequencies of changing frequency, as an FM modulation composition set, applied thereto in succession for respective periods of time.

In one embodiment one or more of the carrier signals are square-wave signals.

In one embodiment one or more of the carrier signals are triangular-wave signals.

In one embodiment one or more of the carrier signals are sinusoidal-wave signals.

In one embodiment the frequency of one or more of the carrier signals is from about 5 MHz to about 13 MHz.

In one embodiment the frequency of the one or more carrier signals is from about 100 MHz to about 500 MHz.

In one embodiment the frequency of the one or more carrier signals is from about 2.3 GHz to about 3.2 GHz.

In one embodiment the one or more carrier signals have a center frequency of about 434 MHz.

In one embodiment the or each AM modulated carrier signal is modulated between a first, low-power state and a second, high-power state, thereby allowing control of power level.

In one embodiment the or each AM modulated carrier signal is modulated with an applied frequency of from about 1 Hz to about 2.6 MHz, optionally about 1 Hz to about 1 MHz.

In one embodiment the or each FM modulated carrier signal is modulated with an applied frequency of from about 1 Hz to about 50 kHz MHz, optionally about 1 Hz to about 10 kHz, optionally about 1 Hz to about 1 kHz.

In another aspect the present invention provides an apparatus for or method of creating resonant standing waves in biological tissue of a subject in treating spinal intervertebral disc disease (IVDD) or musculo-skeletal disorders, pain management and/or tissue regeneration, comprising applying AM modulated and FM modulated carrier signals simultaneously to a subject in order to create resonant standing waves in the tissue.

In a further aspect the present invention provides an apparatus for or method of creating resonant standing waves in biological tissue of a subject in treating anti-inflammatory and/or neurological disorders, comprising applying AM modulated and FM modulated carrier signals simultaneously to a subject in order to create resonant standing waves in the tissue.

In a still further aspect the present invention provides an apparatus for or method of creating resonant standing waves in biological tissue of a subject in treating oncological disorders, in particular tumors, comprising applying AM modulated and FM modulated carrier signals simultaneously to a subject in order to create resonant standing waves in the tissue.

In a yet further aspect the present invention provides an apparatus for or method of creating resonant standing waves in biological tissue of a subject in treating mastitis, in particular bovine mastitis, comprising applying AM modulated and FM modulated carrier signals simultaneously to a subject in order to create resonant standing waves in the tissue.

In yet another aspect the present invention provides an apparatus for or method of creating resonant standing waves in biological tissue of a subject in wound and/or bone healing, comprising applying AM modulated and FM modulated carrier signals simultaneously to a subject in order to create resonant standing waves in the tissue.

In a still yet further aspect the present invention provides an apparatus for or method of creating resonant standing waves in biological tissue of a subject in treating body stones or calcifications, in particular renal and bladder stones, comprising applying AM modulated and FM modulated carrier signals simultaneously to a subject in order to create resonant standing waves in the tissue.

In one embodiment the AM modulated and FM modulated carrier signals are applied through a single applicator.

In another embodiment the AM modulated and FM modulated carrier signals are applied through a plurality of applicators.

In one embodiment the applicators are arranged in one or more arrays.

In one embodiment a single AM modulated carrier signal is applied to the subject.

In one embodiment the or each AM modulated carrier signal has a plurality of AM modulation frequencies of changing frequency, as an AM modulation composition set, applied thereto in succession for respective periods of time.

In one embodiment a plurality of FM modulated carrier signals are applied simultaneously to the subject.

In one embodiment three different FM modulated carrier signals are applied simultaneously to the subject, as a triplet.

In one embodiment one or more of the FM modulated carrier signals have a plurality of FM modulation frequencies of changing frequency, as an FM modulation composition set, applied thereto in succession for respective periods of time.

In one embodiment one or more of the carrier signals are square-wave signals.

In one embodiment one or more of the carrier signals are triangular-wave signals.

In one embodiment one or more of the carrier signals are sinusoidal-wave signals.

In one embodiment the frequency of one or more of the carrier signals is from about 5 MHz to about 13 MHz.

In one embodiment the frequency of the one or more carrier signals is from about 100 MHz to about 500 MHz.

In one embodiment the frequency of the one or more carrier signals is from about 2.3 GHz to about 3.2 GHz.

In one embodiment the one or more carrier signals have a center frequency of about 434 MHz.

In one embodiment the or each AM modulated carrier signal is modulated between a first, low-power state and a second, high-power state, thereby allowing control of power level.

In one embodiment the or each AM modulated carrier signal is modulated with an applied frequency of from about 1 Hz to about 2.6 MHz, optionally about 1 Hz to about 1 MHz.

In one embodiment the or each FM modulated carrier signal is modulated with an applied frequency of from about 1 Hz to about 50 kHz MHz, optionally about 1 Hz to about 10 kHz, optionally about 1 Hz to about 1 kHz.

BRIEF DESCRIPTION OF THE DRAWINGS

Preferred embodiments of the present invention will now be described hereinbelow by way of example only with reference to the accompanying drawings, in which.

DETAILED DESCRIPTION

The apparatus comprises at least one applicator 103 for application to biological tissue T and a drive unit 105 for driving the at least one applicator 103 simultaneously with AM modulated and FM modulated carrier signals in order to create resonant standing waves in the tissue T.

Figure 1:
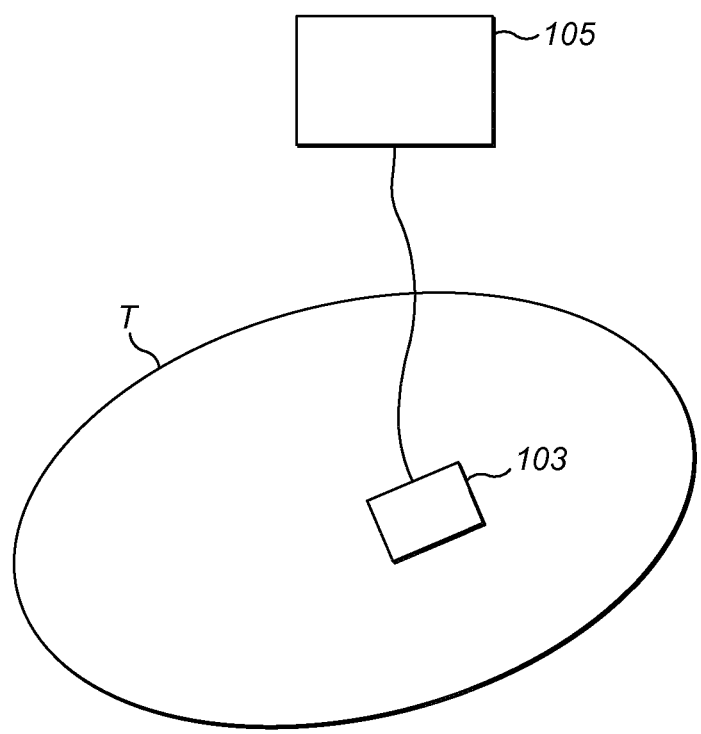
FIG. 1 illustrates an apparatus in accordance with a first embodiment of the present invention.

In one embodiment, as illustrated in FIG. 1, the apparatus comprises a single applicator 103.

Figure 2:
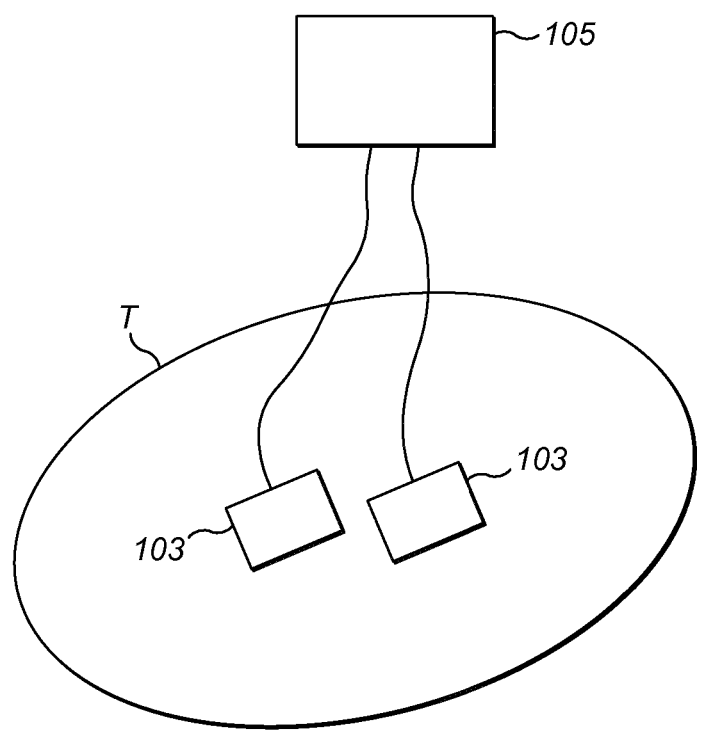
FIG. 2 illustrates an apparatus in accordance with a second embodiment of the present invention.

In one embodiment, as illustrated in FIG. 2, the apparatus comprises a plurality of applicators 103.

Figure 3:
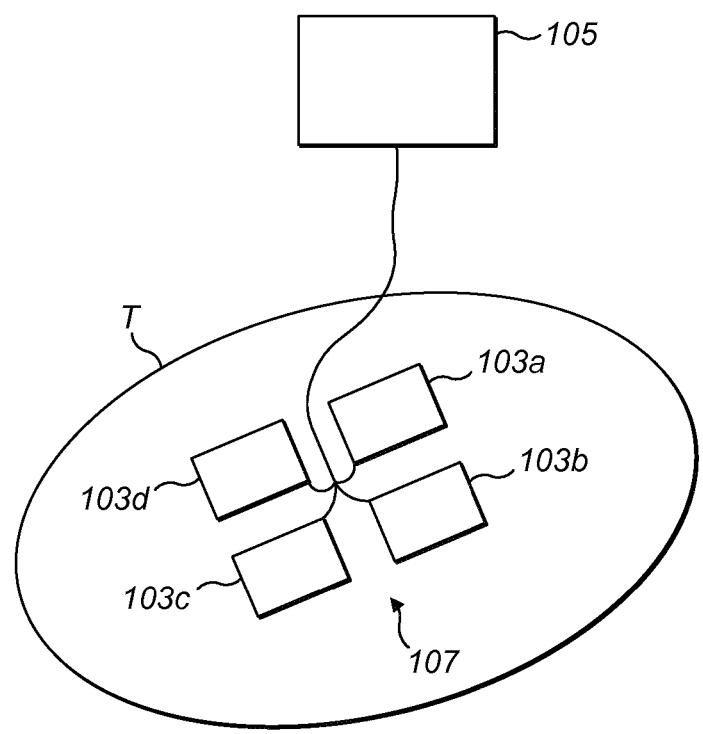
FIG. 3 illustrates an apparatus in accordance with a third embodiment of the present invention.
Figure 4:
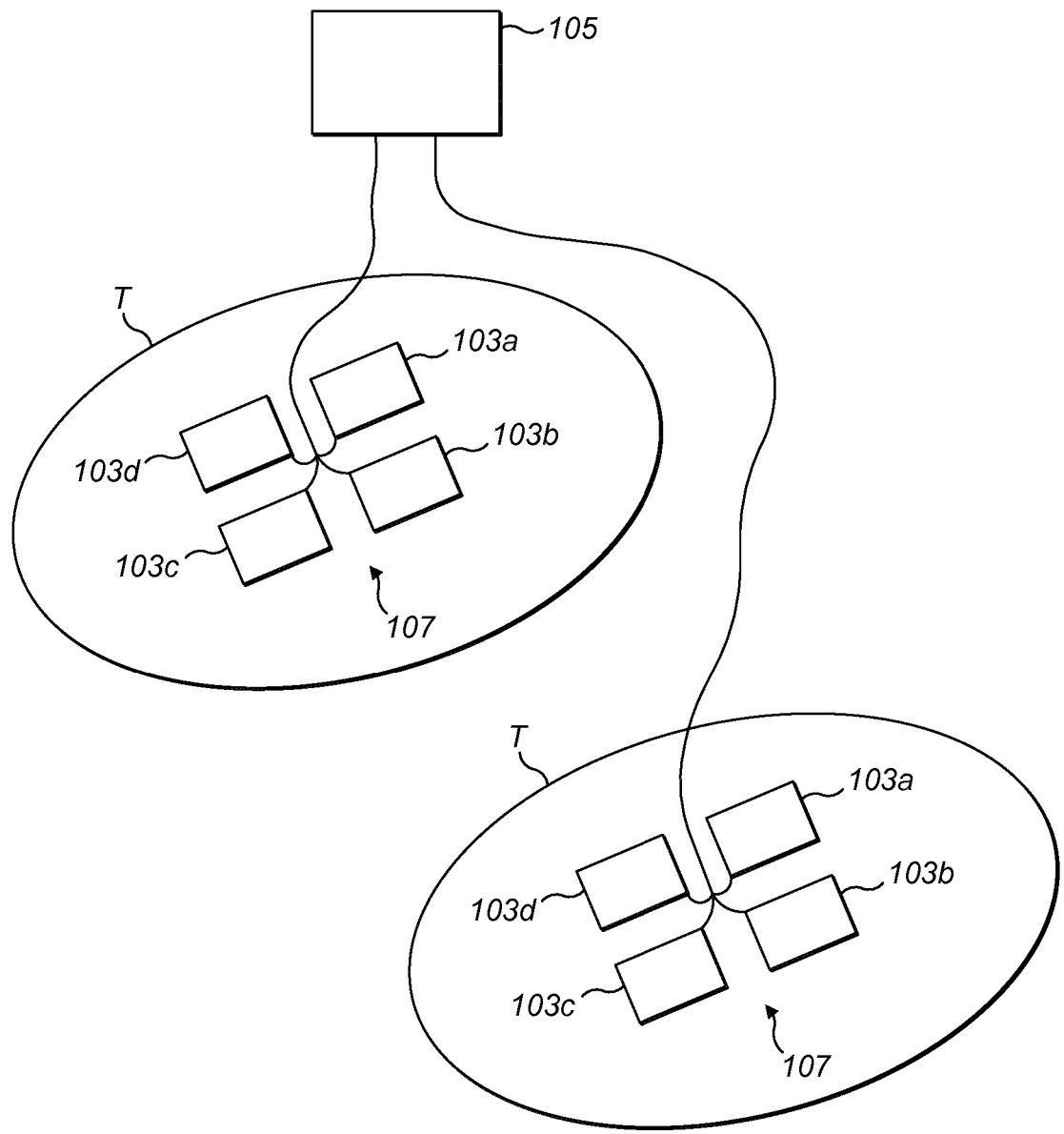
FIG. 4 illustrates an apparatus in accordance with a fourth embodiment of the present invention.

In one embodiment, as illustrated in FIGS. 3 and 4, the applicators 103a-d are arranged in one or more arrays 107.

Figure 5A:
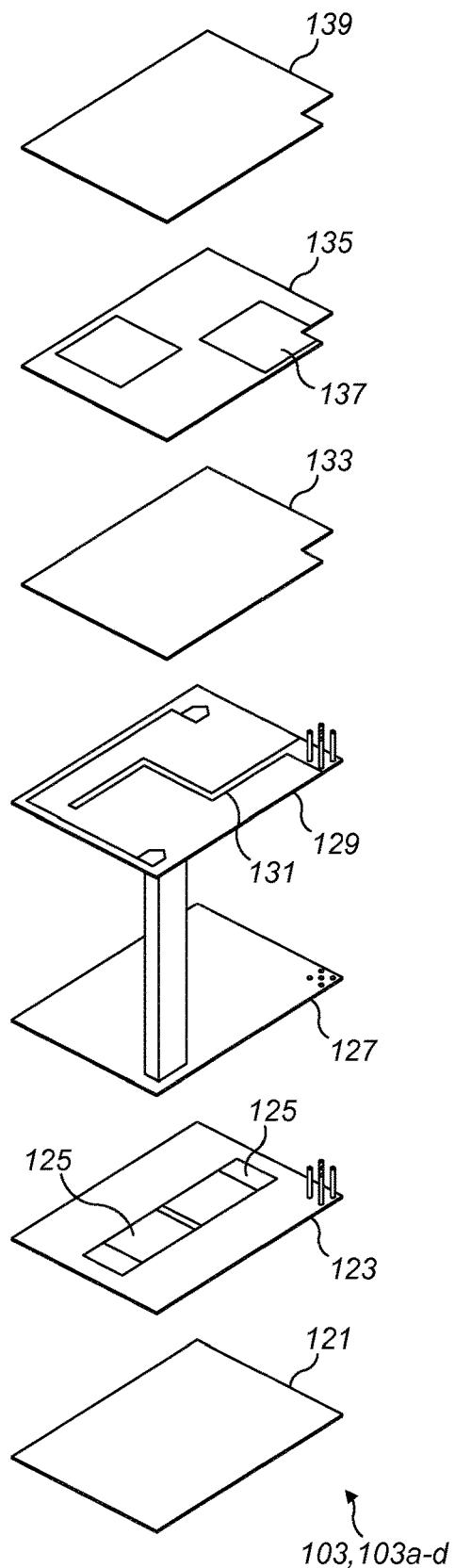
FIGS. 5(a) and (b) illustrate an applicator in accordance with one embodiment of the present invention for use in the apparatus of the present invention.
Figure 5B:
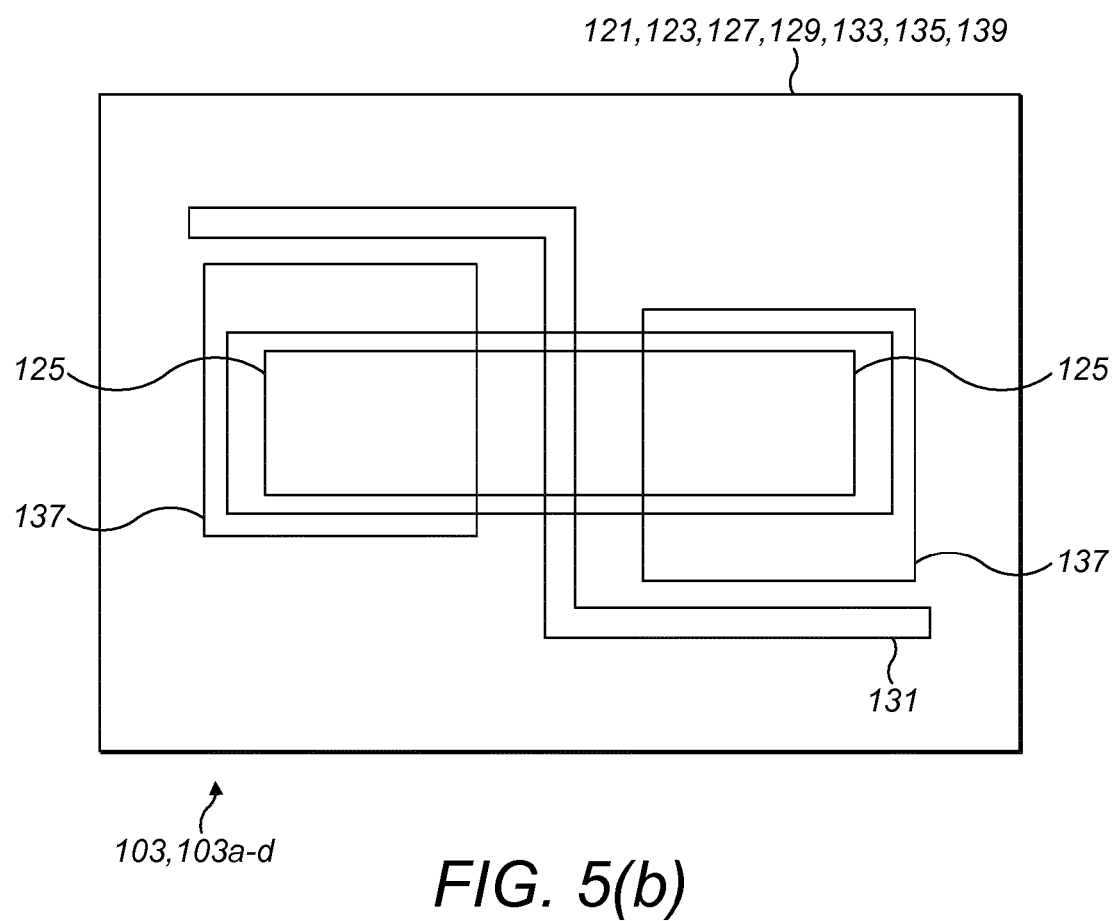

In this embodiment, as illustrated in FIGS. 5(a) and (b), each applicator 103 comprises a first, facing dielectric layer 121 which is applied to the tissue T, a second, director layer 123 which includes coupling slots 125 and overlies the first layer 121, a third, spacing dielectric layer 127 which overlies the second layer 123, a fourth, Z-patch layer 129 which includes a Z-patch 131 and overlies the third layer 127, a fifth, spacing dielectric layer 133 which overlies the fourth layer 129, a sixth, reflector layer 135 which includes a patterned reflector 137 for defining the polarity ratio, and a seventh, absorbing dielectric layer 139 which overlies the sixth layer 135 and provides an electromagnetic (EM) shield.

In one embodiment the or each AM modulated carrier signal has a plurality of AM modulation frequencies of changing frequency, as an AM modulation composition set, applied thereto in succession for respective periods of time.

In one embodiment a plurality of FM modulated carrier signals are applied simultaneously to the at least one applicator 103.

In one embodiment one or more of the FM modulated carrier signals have a plurality of FM modulation frequencies of changing frequency, as an FM modulation composition set, applied thereto in succession for respective periods of time.

In one embodiment the at least one applicator 103 has three different FM modulated carrier signals applied thereto, as a triplet.

In one embodiment one or more of the FM modulated carrier signals have a single FM modulation frequency applied thereto continuously.

In one embodiment one or more of the carrier signals are square-wave signals.

In one embodiment one or more of the carrier signals are triangular-wave signals.

In one embodiment one or more of the carrier signals are sinusoidal-wave signals.

In one embodiment the frequency of one or more of the carrier signals is from about 5 MHz to about 13 MHz.

In another embodiment the frequency of the one or more carrier signals is from about 100 MHz to about 500 MHz.

In a further embodiment the frequency of the one or more carrier signals is from about 2.3 GHz to about 3.2 GHz.

In one embodiment the one or more carrier signals have a center frequency of 434 MHz, with control of AM and FM modulation, power level and duty cycle.

In one embodiment AM modulation allows for power of the associated carrier wave to be modulated between a first, low-power state and a second, high-power state, thereby allowing control of the power level.

Figure 6:
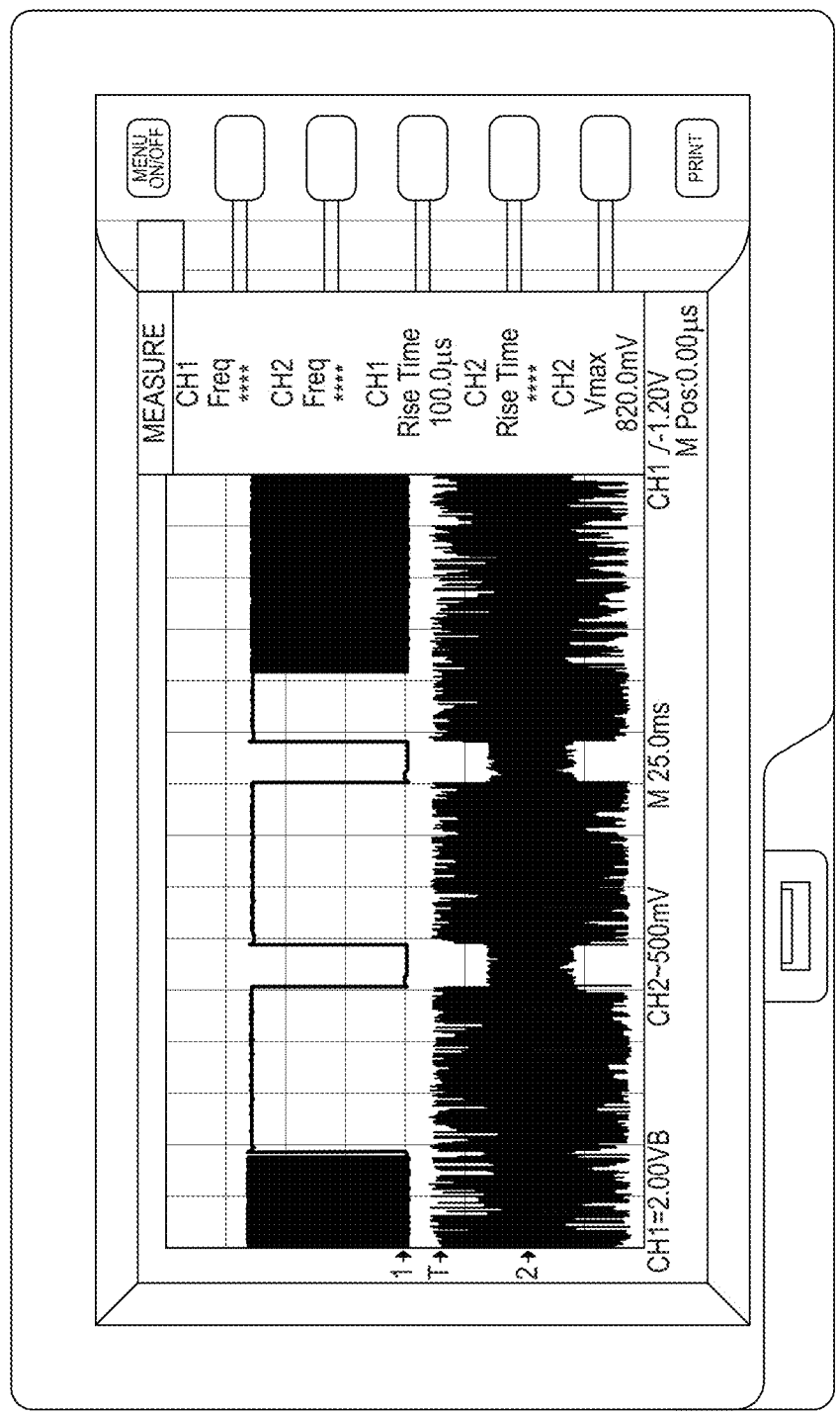
FIG. 6 illustrates one exemplary modulation for the AM modulated carrier signal in accordance with an embodiment of the present invention.

For example, in one embodiment the AM modulated carrier signal can be modulated between a 4 W always-on power state to a 27 W peak power state, with an average power of 11.5 W, as illustrated in FIG. 6.

In one embodiment the or each AM modulated carrier signal is modulated with an applied frequency of from about 0.1 MHz to about 2.6 MHz.

In one embodiment the one or more FM modulated carrier signals are modulated with applied frequencies in the range of from about 0.1 MHz to about 50000 Hz using an audio digital signal.

By applying combinations of frequencies, wave shaping of each carrier signal is achieved, and a series of resonant standing wave configurations can be applied to impart potential energy into water in the biological tissue by manipulation of the water micro-tubular cellular interface, being tuned to match the resonant frequencies of various targeted tissue types, such as organs and glands.

In one embodiment the carrier signals can be pulsated to achieve specific physiological rhythmic effects arising from the effects of standing wave generation and the resonant frequency stimulation of the biological tissue, which are soft glassy materials in kind [Fredburg et al, "The cytoskeleton as a soft glassy material", Cytoskeletal Mechanics: Models and Measurements, pages 3 to 8 (2006)].

The apparatus is capable of applying a wide range of resonant arrangements that deliver clinically-relevant, non-invasive therapies with the purpose of providing electronic, anti-inflammatory and other physiological effects.

Always on Temperature and Frequency Matching

In one embodiment the apparatus is controlled continuously to operate to generate standing waves in biological tissue while operating within a predetermined range of temperature, for example, a temperature ceiling of from about 37° C. to about 41° C.

In this embodiment the power and duty cycle of the AM and FM modulated carrier signals are controlled in order to maintain continuous application of the carrier signals, and so prevent the apparatus from turning off when a target temperature is approached.

In one embodiment the power and duty cycle of the AM and FM modulated carrier signals are controlled to maintain the desired temperature within +/−0.1° C.

With this "always-on" methodology, on-off cycling of the apparatus is avoided when a target temperature is reached, and enables treatment without interruption of the therapy.

Ideal Resonance

In one embodiment the apparatus successively applies a test series of different resonant frequencies to the carrier signals for a predetermined period of time, for example, one minute, and measures the time taken to raise the temperature of the tissue with each specific frequency set, and this time is compared to the temperature rise for each respective frequency set. After this series of test frequency runs, the apparatus selects the most efficient resonant frequency set as determined by the fastest temperature rise in a given amount of time in order to continue the therapy with the ideal resonant frequency for the tissue being treated.

Multiple AM Resonance

In one embodiment multiple applicators 103, for example, as a triplet, are made to play in harmony by offsetting each set of applicators 103 in Fibonacci sequence, or so-called golden "Phi", in order to create a harmonic ratio between all of applicators 103 applied over the area of the body to be energized.

In one embodiment the base frequency of this set is 1.618 Hz and the applicators 103 are driven for a predetermined period of time, for example, from about 1 second to about 10 seconds, then the base frequency is raised by 1.618 Hz, with the applicators again being driven for a predetermined period of time, for example, from about 1 second to about 10 seconds, and this incremental increase in the base frequency is repeated in order to produce an ascending set of harmonic standing waves that efficiently oscillate the tissue.

In one embodiment the base frequency can be made to climb up to a predetermined frequency, for example, about 13000 Hz or about 2.6 MHz.

In one embodiment, once the predetermined frequency is attained, the ascending harmonic is repeated.

Multiple Audio Digital Signal Generators

In one embodiment a plurality of FM modulated carrier signals are applied simultaneously over an AM modulated carrier signal.

In one embodiment the rate of modulation of each FM modulated carrier signal can be different over each of a plurality of ranges of frequency.

In one embodiment the FM modulated carrier signals can be made to modulate at a first, slow rate at a frequency of less than from about 1 Hz to about 10 Hz, for example, at 1 Hz or 7.83 Hz.

In one embodiment the FM modulated carrier signals are made to be offset by a 1.618033 ratio in Fibonacci sequence to each other in order to form a harmonic standing wave that will ascend by increasing the base frequency by 1.618 Hz, and applied for a predetermined period of time, for example, from about 1 second to about 10 seconds.

In one embodiment the base frequency can be made to climb up to a predetermined frequency, for example, about 20000 Hz.

In one embodiment, once the predetermined frequency is attained, the ascending harmonic is repeated.

Various tuning ratios are possible for the arrangement by thirds, fifths, sevenths and Pythagorean, for harmonic oscillatory stimulation of the biological tissue in contact with the applicator 103.

Multiple Audio Digital Signal Generators and Binaural Beats Combinations

In one embodiment the FM modulated carrier signals may be offset by from about 0 Hz to about 3 Hz, from about 5 Hz to about 8 Hz, from about 8 Hz to about 13 Hz and from about 13 Hz to about 33 Hz in order to create an oscillatory effect such as experienced with binaural beats.

For example, in a triplet, one audio signal can applied at 174 Hz and the other two audio signals can be applied at 528 Hz and 529.6 Hz. This arrangement provides a low-frequency harmonic drone with a binaural pulsing of 2.6 Hz between the 528 Hz and 529.6 Hz frequencies. The net effect is to augment the energy delivered to the target area with a binaural rhythmic stimulation at 2.6 Hz, which can be used to entrain the brain with waves of any desired frequency as user specified when placed over the cerebrum or other parts of the brain.

In preferred embodiments the energy transferred by the standing waves generated by the one or more applicators 103 in the tissue is used to increase the potential energy of the water inside of the mitochondria in the tissue under the applicator. This energy can convert ADP into ATP and NAD into NADH through the conversion of ionic standing wave oscillation of the water molecules inside of the mitochondria and tissues into potential energy for charge separation and the creation of ordered structured water along hydrophilic surfaces.

In preferred embodiments the apparatus produces standing waves in tissues that are powerful stimulators of mechanotransduction in vivo, which influence integrin dynamics and cause force-dependent effects such as endothelial responses to shear stress and the regulation of growth and gene expression in many tissues through forced oscillations.

Heat Shock Protein Production

In preferred embodiments the apparatus augments the electromagnetic stimulation of biological tissue through resonance in order to stimulate the tissue into the production of heat shock protein (HSP), such as gp96, hsp70 and hsp90 in vivo.

HSPs have been disclosed, for example, in US-A-2003/0012793, positively to effect biological tissue specifically with regards to the rehabilitation of neurologic tissue, wounds, fractures, organs such as the heart, lungs, liver, spleen, kidneys, stomach, small and large intestines, prostate, testes, ovaries, adrenal glands, thyroid glands, pituitary glands, brain, eyes, spinal cord, peripheral nerves, tendons, ligaments, cartilage, bones, hair, nails and skin.

Heat Shock Factor

In one embodiment the apparatus can be utilized to perform local ultra-high frequency resonant hyperthermia, in order to stimulate donor sites for cancer vaccines.

In one embodiment donor sites are prepared for a predetermined period of time, for example, from about 30 minutes to about 60 minutes, prior to vaccine delivery intradermally to prepare dendritic cells for immunization.

In another embodiment the apparatus can be utilized to perform local ultra-high frequency resonant hyperthermia of solid tumors alone or in combination with supraparamagnetic iron oxide nanoparticles (SPIONs) of various sizes and in metamaterial combinations of, for example, from about 5 nm to about 30 nm, carboplatin, cisplatin, 2-desoxy-D-glucose and dl-glyceraldehyde, and other chemotherapeutic agents.

Localized tumor hyperthermia (LTH) has been disclosed potentially to serve as a source of tumor antigen, where dying apoptotic/necrotic cells release tumor peptides slowly over time, and additionally LTH-treated cells can release HSPs that can chaperone antigenic peptides to antigen-presenting cells, such as dendritic cells [Mukhopadhaya et al, "Localized Hyperthermia Combined with Intratumoral Dendritic Cells Induces Systemic Antitumor Immunity", Cancer Res., 67(16), pages 7798-7806 (2007).

In addition, cytoprotection can be offered by electromagnetic (EM) field induction of stress proteins [Carmody et al, Journal of Cellular Biochemistry, 79(3), pages 453-459 (2000)].

Stimulation of human promyelocytic HL60 cells by a magnetic field at normal growth temperatures has been disclosed to result in heat shock factor 1 activation and heat shock element binding, a sequence of events that mediates the stress-induced transcription of the stress gene hsp70 and increased synthesis of the stress response protein hsp70kD [Lin et al, Electromagnetic field exposure induces rapid, transitory heat shock factor activation in human cells, J. Cell. Biochem., 66, pages 482-488, 1997].

Pain Relief

Nerve conduction block induced by high-frequency biphasic rectangular pulses has been disclosed [Zhang et al, IEEE Transactions on Biomedical Engineering, 53(7), pages 1433-1436 (2006)]. At the temperature of 37° C., axons of different diameters (2-20 µm) can be blocked completely at supra-threshold intensities when the stimulation frequency is above 10 kHz.

Example

Nerve blocking and pain relief has been demonstrated by application of the following AM and FM modulations in repetition.

Figure 7:
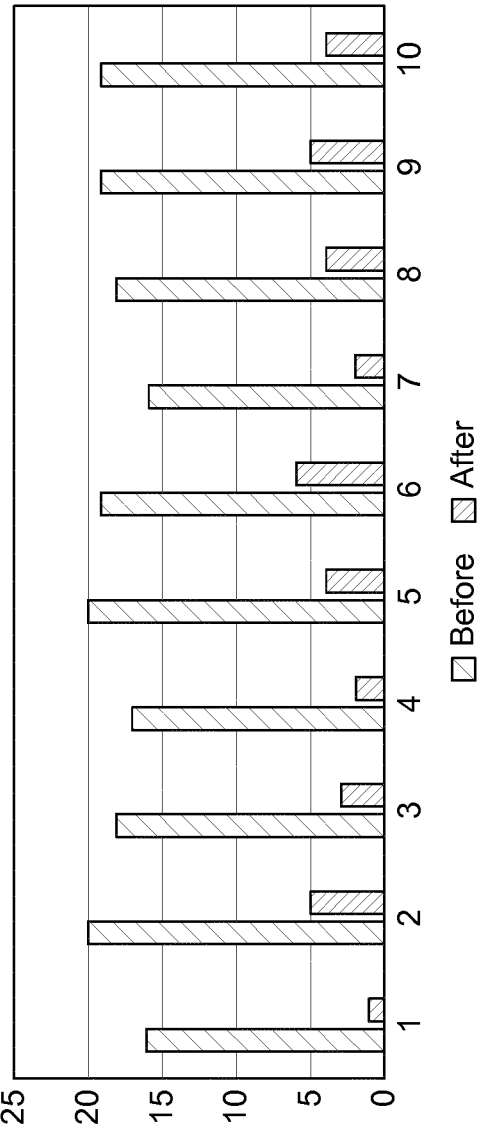
FIG. 7 illustrates a plot of nerve blocking and pain relief scores in subjects following application of AM and FM modulations in repetition in accordance with one embodiment of the present invention.

AM Modulation:
13000 Hz
21000 Hz
10000 Hz
34000 Hz
50,000 Hz
then repeat
FM Modulation (audio digital signal):
10000 Hz
13000 Hz
21000 Hz
34000 Hz
50000 Hz
repeat all 3 tones offset and played in a round The pain relief scores using this treatment regime are shown in FIG. 7.

Nerve Blocking and Potential Pain Relief

The frequency composition of 2T1 increases hsp70 and hsp27 in neurological tissue. Franklin et al, "The role of heat shock proteins Hsp70 and Hsp27 in cellular protection of the central nervous system", International Journal of Hyperthermia, 21(5), pages 379 to 392 (2005) disclose the potential for manipulating the expression levels of HSPs for therapeutic advantage in neurodegenerative diseases, such as Alzheimer's disease, stroke and glaucoma. Expression in the brain of two HSPs, the 70 kDa HSP (hsp70) and the 27 kDa HSP (hsp27), is notable because both proteins are highly inducible in glial cells and neurons following a wide range of noxious stimuli including ischemia, epileptic seizure and hyperthermia. In the central nervous system, constitutive expression of hsp27 is limited to many (but not all) sensory and motor neurons of the brain stem and spinal cord, while there is little or no constitutive expression of hsp70. However, inducible expression of both hsp70 and hsp27 is present in many areas of the brain and retina and is associated with cellular resistance to a variety of insults.

The apparatus can be employed as a method to induce hsp70 and hsp27 expression non-invasively in neurological tissue.

Ponderomotive Force

The apparatus is employed to apply a ponderomotive force, being a non-linear force that a charged particle experiences in an inhomogeneous oscillating electromagnetic field, locally over a biological or non-biological material in order to lower the density of the material while the apparatus is stimulating the target material. The apparatus is tuned to biological tissues and the ponderomotive force is employed to decrease the density and viscosity of the same tissues, which increases the thixotropic rate of thick gels or fluids under the at least one applicator 103 for the purpose of biological stimulation.

When the biologic soft glassy materials under the at least one applicator 103 are stimulated and oscillated by the standing waves it allows for the "rejuvenation" (uniform agitation and distribution) of these materials and facilitates the removal of intracellular debris and toxins from them non-invasively.

Stimulation and Rejuvenation of Soft Glassy Materials Using Ionic Standing Wave Generation In one embodiment the apparatus can be used to stimulate and rejuvenate soft glassy materials such as biological tissue with oscillating standing waves of various AM modulations and one or more FM modulated carrier signals. Modulated stimulation generated by audio-to-digital sound generators increases the oscillation and agitation of biological soft glassy materials and promotes the thixotropic properties of the soft glassy material composed of water, microtubules, membrane bilayers, proteins and intracellular organelles, cells in general as stimulated locally. The standing waves generated by the apparatus affect the thixotropic properties of water especially along biological and other polymer gels.

Water along hydrophilic surfaces, micro-tubular networks and intracellular water tend to gel and stiffen up over time, as well as become contaminated with metabolic debris, waste products and toxins. The cyclotron ionic stimulation and rhythmic standing wave oscillation of the water and biological tissues generated under the at least one applicator 103 are made mechanically to vibrate the soft glassy material that is the intracellular milieu and cause the soft glassy material that is the cells, tissue and water to become thixotropic. That is, the gelled ordered structured water begins to become thin and less viscous over time when shaken and oscillated by the AM modulation and FM modulated standing waves generated by the apparatus. When the biologic soft glassy materials under the applicator 103 are stimulated and oscillated by the standing waves, the stimulation allows for the "rejuvenation" (uniform agitation and distribution) of these materials and facilitates the removal of intracellular debris and toxins from them non-invasively. After the oscillating energy is turned off the potential energy of vibration is used by the water in the cells to create ordered structured water and to facilitate the separation of charges along hydrophilic surfaces into negative charges close to the hydrophilic surface, with positive charges just outside the negative EZ Water layer zone formed along the hydrophilic surface.

Example

Stimulation and rejuvenation of soft glassy materials has been demonstrated by application of the following AM and FM modulations in repetition.
AM Modulation:
10 Hz
13000 Hz
42000 Hz
500000 Hz
1 MHz, each for 3 seconds
then repeat
FM Modulation:
Signal 1.
528 Hz continuously
Signal 2
1056 Hz continuously
Signal 3
2108 Hz continuously Example An 18 inch tall×24 inch long×18 inch wide tank was filled with 10 inches of muscle phantom gel. A ruler was placed along the length of the tank to measure the distance of transfer of heat. The experiment started at a temperature of 9.1° C. and an applicator pad was placed on the outside for 1 hour. The tank reached a maximum of 31° C. and a depth of penetration was 15 cm against cold gel. Visuals of depth of penetration are shown in Figure AA, with progress being shown from left to right.

Figure 8:
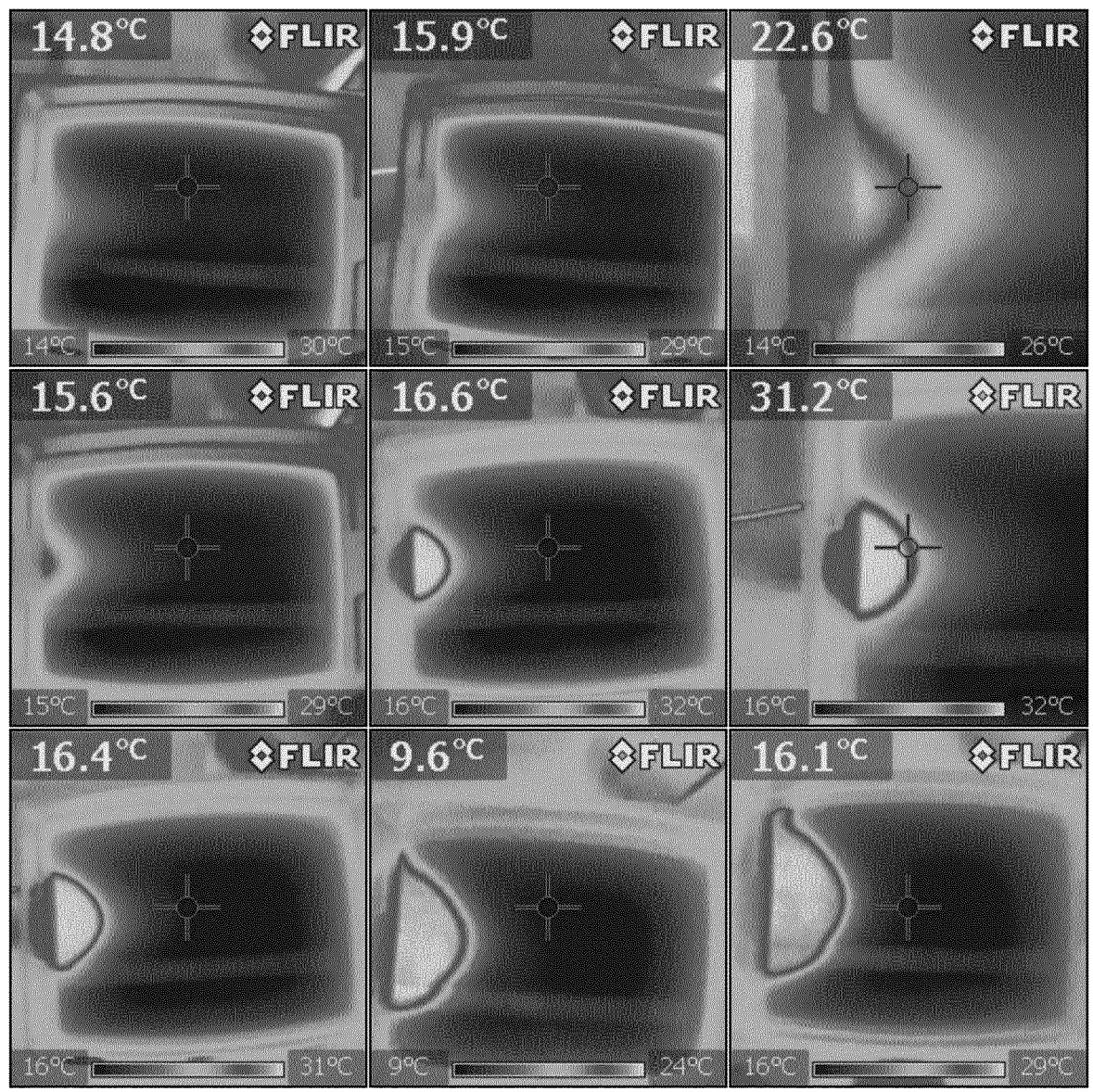
FIG. 8 illustrates images of the thixotropic and thermal rise in muscle phantom following application of AM and FM modulations in repetition in accordance with one embodiment of the present invention.

FIG. 8 illustrates the thixotropic and thermal rise demonstrated in muscle phantom. With external application of an applicator to the tank, the area of thixotropic response extends for greater than 15 cm with 15 minutes of therapy.

Example

A one gallon milk jug was filled with cold load phantom gel (dimensions: 9¾ inches high, and a square base of 5¾ inches by 5¾ inches). An applicator pad was placed on the bottom of the jug for one hour. The initial temperature was 70° F. and a maximum temperature of 101° F. was reached after over an hour. The heat completely penetrated throughout the whole milk jug.

Figure 9:
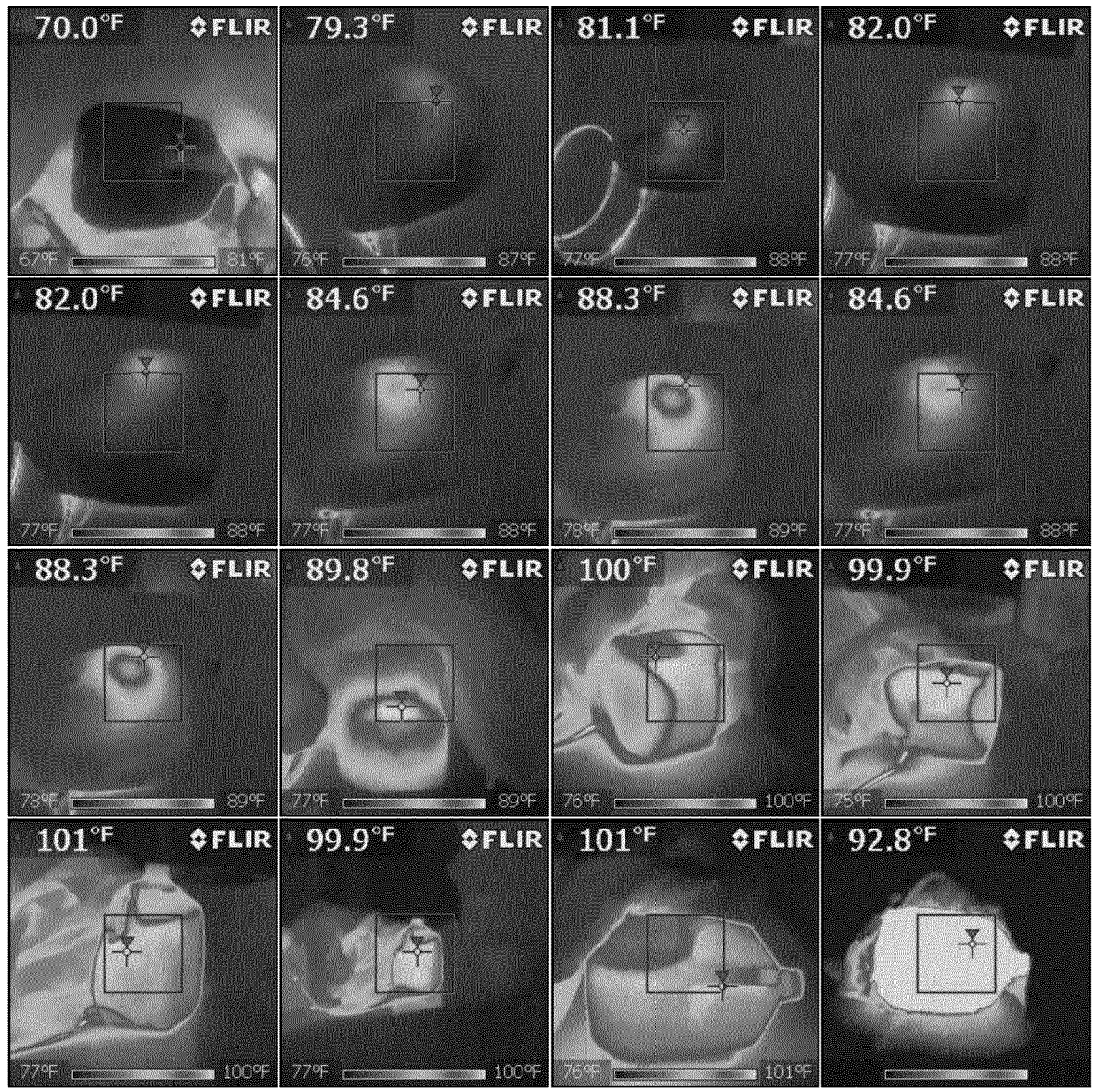
FIG. 9 illustrates images of the thixotropic and thermal rise in muscle phantom following application of AM and FM modulations in repetition in accordance with another embodiment of the present invention.

FIG. 9 illustrates the thixotropic and thermal rise demonstrated in the phantom.

Neurological

In one embodiment the apparatus creates standing waves in tissue to decrease local edema of the tissue by oscillating the edematous tissue and forcing a phase change of water from liquid $H_2O$ into liquid crystal $H_3O_2$, known as EZ water, along hydrophilic surfaces.

The oscillation increases the potential energy of the edematous water found in the tissues and forces the same to separate charges into positive and negative along hydrophilic surfaces and to assemble into ordered structured EZ water along the same hydrophilic surfaces. The effect is a decrease in edema in the tissues under the applicator.

In one embodiment the at least one applicator 103 can be used as a means to deliver a neurological set of standing waves for the specific intention of decreasing edema, increasing blood flow and oxygenation of neurological tissues and to enhance the production of HSPs in situ local regionally under the at least one applicator 103.

In one embodiment the apparatus is used to create standing waves and electromagnetic stimulation of neurological tissue such as the brain, spinal cord and peripheral nerves in vivo, with the or each applicator 103 being positioned over the brain in order to stimulate the brain with standing waves having a frequency of from about 3 Hz to about 13 Hz, so producing neuro-protective HSPs in the brain and increasing blood flow and oxygen delivery to the same tissues.

Seizure Disorder

In one embodiment the apparatus is used as a method to decrease the severity of seizure disorder and to treat seizure disorder through the stimulation of HSPs.

Depression

In one embodiment the apparatus is used to treat depression by the stimulation of the left frontal lobe and other areas of the brain.

Example

In one Example, the left frontal lobe is treated for 15 minutes with a target temperature of 37° C., three times per week for four weeks, and an increase in blood flow and delivery of oxygen to the neurological tissue being stimulated has been demonstrated.

Parkinson's

In one embodiment the apparatus is used to treat the symptoms of Parkinson's disease by increasing blood flow and oxygen delivery to the cerebellum and by the production of the neuro-protective chemicals hsp70 and hsp27 in the cerebellum and the production of L-Dopa in the Substantia Nigra.

Blood Brain Barrier (BBB)

In one embodiment the apparatus is used as a method to open the blood brain barrier for clinical application.

In one embodiment the or each applicator 103 is placed behind the neck and skull of a patient and oscillated with a set of neurologically-enhancing frequencies for a predetermined period of time, for example, from about 20 minutes to about 30 minutes.

Alzheimer's

In one embodiment the apparatus provides for the treatment of Alzheimer's disease by allowing the glial cells to enhance removal of amyloid from neurological tissue, potentially reversing the clinical signs and progression of the disease. The oscillatory effect, as disclosed hereinabove, also enhances the removal of intracellular toxins, cellular mediators of inflammation and unwanted protein derived debris from neurological tissue.

Dominant Frequency Entrainment

In one embodiment the apparatus creates standing waves in the brain to entrain the brain with a dominant frequency in the delta, alpha, theta and/or beta brain wave EEG frequency ranges.

In one embodiment a frequency of 2.5 Hz in the delta frequency range is employed to entrain the brain into a calm state.

In one embodiment a frequency of 7.82 Hz in the theta frequency range is employed to create an alert and awake state.

Neurological Rehabilitation

In one embodiment a set of frequencies are applied to one or more applicators placed over an area of neurological injury at periodic intervals for a period of time, for example, for about 20 minutes to about 30 minutes every other day or once weekly for period of about 4 to 6 weeks.

The electromagnetic heating promotes the production of HSPs, in particular hsp70 and hsp90. As discussed above, hsp70 has been found to be neuro-protective and a promoter of neurological rehabilitation.

In this embodiment a series of AM modulated standing square waves are applied in succession which are selected from frequencies of from about 7.82 Hz to about 13 Hz, from about 15 Hz to about 17 Hz, from about 54 Hz to about 56 Hz, about 108 Hz, from about 500 Hz to about 2000 Hz, from about 2000 Hz to about 15000 Hz, from about 15000 Hz to about 1 MHz, and from about 1 MHz to about 2.6 MHz, in combination with FM modulated standing square waves in succession which are selected from frequencies of from about 7.82 Hz to about 13 Hz, from about 15 Hz to about 17 Hz, from about 54 Hz to about 56 Hz, about 108 Hz, and from about 500 Hz to about 528 Hz.

Frequencies in the range of about 7.82 Hz to about 13 Hz, and in particular about 10 Hz, can promote neurological rehabilitation.

Frequencies in the range of about 16 Hz to about 55 Hz can promote calcium movement in neurologic tissue.

Frequencies in the range of about 10000 Hz to 2.6 MHz can promote pain relief.

Implants

In one embodiment the apparatus is used to activate dynamically and reversibly tunable implant structures, such as polymer implants.

In one embodiment the implant includes a nanobiological target to be utilized as a manipulative hyperthermia material stimulator.

In another embodiment the implant includes a switchable drug release platform by stimulating the implanted or injected target material, for example, a nanolipid ball filled with doxorubicin, with an array of standing waves locally at the target tissue and implanted nanotarget.

Ionic Movement/Chemical Reaction

In one embodiment the apparatus comprises frequency compositions which enhance ionic movement within cells, thus enhancing ionic movement and chemical reactions in the area energized by the apparatus.

Example—Neurological Rehabilitation (2T1)

One example of a neurological rehabilitative frequency composition is as follows:
AM modulation:
3.0 Hz for 10 seconds
7.82 Hz for 10 seconds
10 Hz for 10 seconds
16 Hz for 10 seconds
10 Hz for 10 seconds
55 Hz for 10 seconds
10 Hz for 10 seconds
108 Hz for 10 seconds
10 Hz for 10 seconds
500 Hz for 10 seconds
10 Hz for 5 seconds
880 Hz for 5 seconds
10 Hz for 10 seconds
1577 Hz for 5 seconds
10 Hz for 10 seconds
3000 Hz for 5 seconds
10 Hz for 10 seconds
5000 Hz for 5 seconds
10 Hz for 10 seconds
10000 Hz for 5 seconds
10 Hz for 10 seconds
13000 Hz for 5 seconds
then repeat
FM Modulation:
Mode #1
The application of three FM modulation signal frequencies:
Signal 1
528 Hz continuously
Signal 2
526.6 Hz continuously
Signal 3
174 Hz for 10 seconds
263.3 Hz for 10 seconds
350.4 Hz for 10 seconds
533.3 Hz for 10 seconds
639 Hz for 10 seconds
963 Hz for 10 seconds
then repeat in a round
In one embodiment each frequency component can be applied from about 3 s to about 10 s.
Mode #2
In this Example, the FM modulation applies a three chord combination at the same time, as follows.
Signal 1
174 Hz for 10 seconds
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
then repeat
Signal 2
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
then repeat
Signal 3
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
285 Hz for 10 seconds
then repeat In one Example, this neurological composition was employed in the rehabilitation of dogs from paralysis and paresis due to vertebral disk disease.

Target temperatures of between 37° C. and 41° C. were achieved over the area of pathology within 10 to 15 minutes, and stimulation over the area of tissue was maintained for 10 minutes.

Immediate improvement in deep and superficial pain responses were noted after the therapy.

Therapy was delivered once or twice per week for 2 to 4 weeks. Dogs were given a range of from 2 to 6 treatments. Pain scores were taken before the first treatment and after the last treatment; the worst possible score being 20, and the best possible score being 0.

Figure 10:
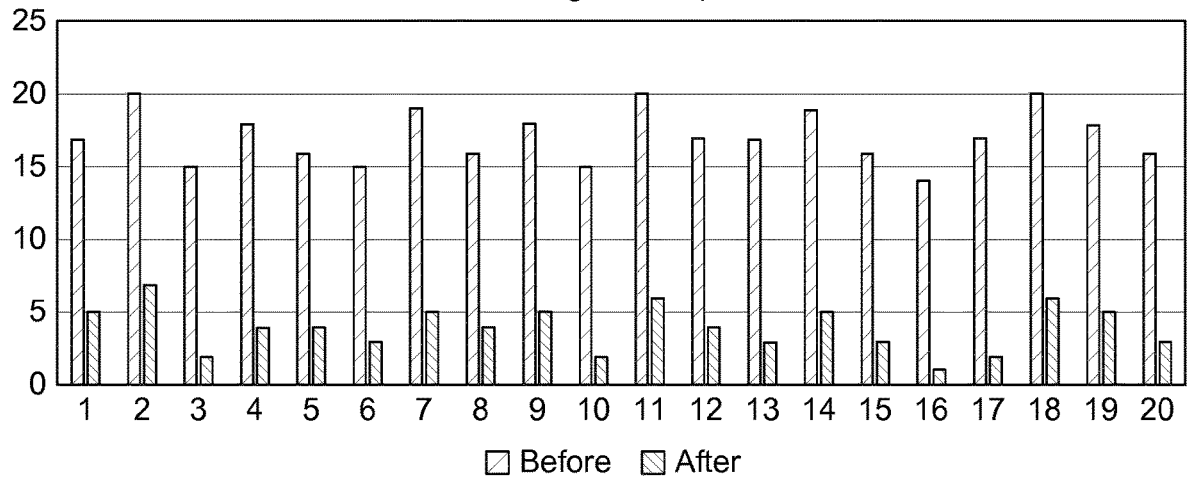
FIG. 10 illustrates a plot of neurological rehabilitation scores in subjects following application of AM and FM modulations in repetition in accordance with one embodiment of the present invention.

The pain scores are shown in FIG. 10. As will be seen, each of the dogs exhibited a marked improvement following treatment.

Example—Pain Relief (2T2)

One example of a neurological rehabilitative frequency composition is as follows:
AM modulation:
Mode #1
7.82 Hz for 10 seconds
1 MHz for 5 seconds
10 Hz for 10 seconds
2 MHz for 5 seconds
10 Hz for 10 seconds
13000 Hz for 10 seconds
10 Hz for 10 seconds
10000 Hz for 10 seconds
500 Hz for 10 seconds
10 Hz for 10 seconds
13000 Hz for 5 seconds
10 Hz for 10 seconds
3000 Hz for 5 seconds
10 Hz for 10 seconds
5000 Hz for 5 seconds
10 Hz for 10 seconds
10000 Hz for 5 seconds
then repeat
Mode #2
3.0 Hz for 10 seconds
7.82 Hz for 10 seconds
10 Hz for 10 seconds
16 Hz for 10 seconds
10 Hz for 10 seconds
55 Hz for 10 seconds
10 Hz for 10 seconds
108 Hz for 10 seconds
10 Hz for 10 seconds 500 Hz for 10 seconds
727 Hz for 5 seconds
787 Hz for 5 seconds
880 Hz for 5 seconds
10 Hz for 10 seconds
1577 Hz for 5 seconds
10 Hz for 10 seconds
3000 Hz for 5 seconds
10 Hz for 10 seconds
5000 Hz for 5 seconds
10 Hz for 10 seconds
10000 Hz for 5 seconds
then repeat from 7.82 Hz
Mode #3
This mode of AM modulation is a temperature-regulated mode.
7.82 Hz until 37° C.
then
10 Hz until 38° C.
then
3.0 Hz for 3 seconds
7.82 Hz for 3 seconds
10 Hz for 3 seconds
16 Hz for 2 seconds
10 Hz for 3 seconds
55 Hz for 2 seconds
10 Hz for 3 seconds
108 Hz for 2 seconds
10 Hz for 3 seconds
500 Hz for 1 second
727 Hz for 1 second
787 Hz for 1 second
880 Hz for 1 second
10 Hz for 3 seconds
1577 Hz for 1 second
10 Hz for 3 seconds
3000 Hz for 2 seconds
10 Hz for 3 seconds
5000 Hz for 2 seconds
10 Hz for 3 seconds
10000 Hz for 1 second
3.0 Hz for 2 seconds
7.82 Hz for 3 seconds
10 Hz for 3 seconds
16 Hz for 3 seconds
10 Hz for 3 seconds
55 Hz for 2 seconds
10 Hz for 3 seconds
108 Hz for 2 seconds
10 Hz for 3 seconds
500 Hz for 1 second
727 Hz for 1 second
787 Hz for 1 second
880 Hz for 1 second
10 Hz for 3 seconds
1577 Hz for 3 seconds
10 Hz for 3 seconds
3000 Hz for 2 seconds
10 Hz for 3 seconds
5000 Hz for 2 seconds
10 Hz for 3 seconds
10000 Hz for 2 seconds
then repeat
If the temperature drops below 38° C., then 10 Hz is applied until 38° C. is reached, and the above repetitive composition is resumed.

If a target temperature of 41° C. is reached, power is reduced.

FM modulation:

In this Example, the FM modulation applies a three chord combination at the same time, as follows.
Signal 1
528 Hz continuously
Signal 2
526 Hz continuously
Signal 3
174 Hz for 10 seconds
263.3 Hz for 10 seconds
350.4 Hz for 10 seconds
533.3 Hz for 10 seconds
639 Hz for 10 seconds
963 Hz for 10 seconds
then repeat in a round Example Following treatment with the above composition, a dog which was not able to stand and lacked deep and superficial pain, was able to regain function after one treatment after a week's time, being able to run around immediately after the second treatment.

Example

Dogs tested for a variety of painful conditions were treated with the above composition. Each dog was given a range of from 2 to 6 treatments, and scores were taken before the first treatment and after the last treatment; the worst possible score being 20 and the best possible score being 0.

Figure 11:
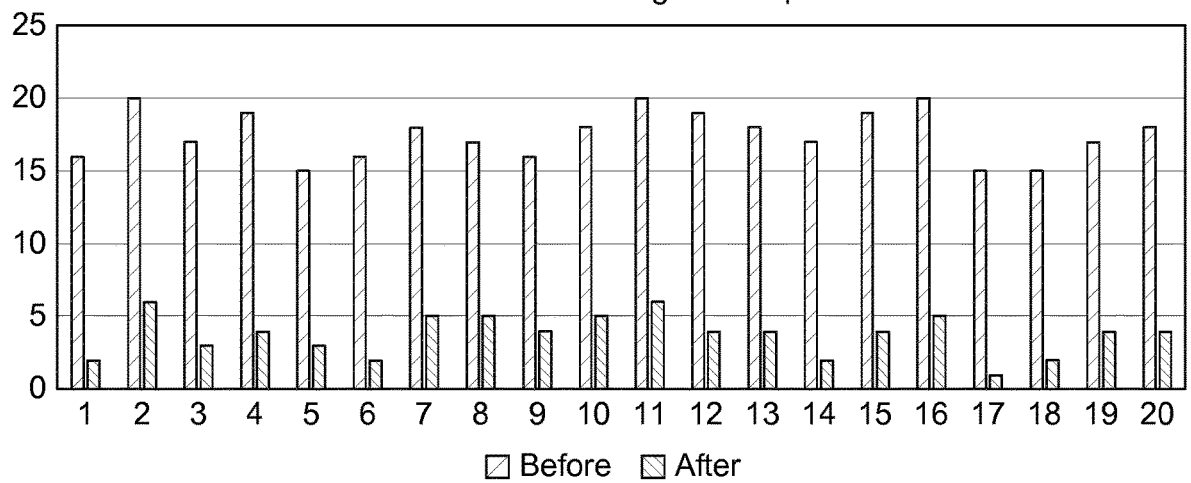
FIG. 11 illustrates a plot of pain scores in subjects following application of AM and FM modulations in repetition in accordance with one embodiment of the present invention.

Following 15 minutes to 30 minutes of stimulation over the painful area, the pain scores were lowered on average by 50 to 80% of the original pain score, as shown in FIG. 11, with many animals having pain scores return to 0% immediately after the therapy. Animals with chronic pain were treated once or twice weekly and showed continuous improvement in pain scores and range of motion when associated with arthritis in a particular joint.

Wound Rehabilitation

The apparatus applies the above 2T2 composition in wound repair, with the or each applicator 103 being applied to the wound injury for 20 to 30 minutes every other day or once weekly for 4 to 6 weeks.

Frequencies in the range of from 22 to 27 Hz can promote collagen synthesis.

A frequency of 108 Hz can provide for treatment of edema.

Frequencies in the range of from 500 Hz to 13000 Hz can provide for pain mitigation.

Example

Figure 12:
FIG. 12 illustrates images showing the epithelialization of the hard palate of a subject following application of AM and FM modulations in repetition in accordance with one embodiment of the present invention.
Figure 12:
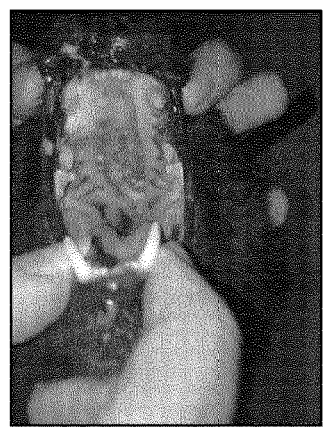
Figure 12:
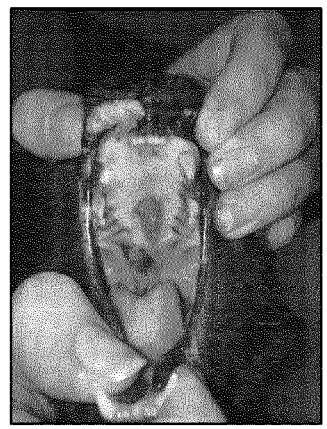
Figure 12:

A feline patient with eosinophilic granuloma complex of the hard palate, and which was unresponsive to years of steroidal standard level care, showed epithelialization of the hard palate over a three-month period using this composition, as shown in FIG. 12. This 18-year old female cat had been treated for four years with depo Medrol monthly injections on presentation. Results for re-epithelialization are over a three month period, 1 hour therapy once weekly for 8 weeks, and then every 2 weeks for one more month. This patient is stable to date.

HSP production is attributed to the observed results, as well as multiple mechanisms of action, such as hyperthermia induced vasodilation with its subsequent increase in blood flow, oxygen and plasma protein rich reparative molecules and other humoral regenerative substances.

Example

Figure 13:
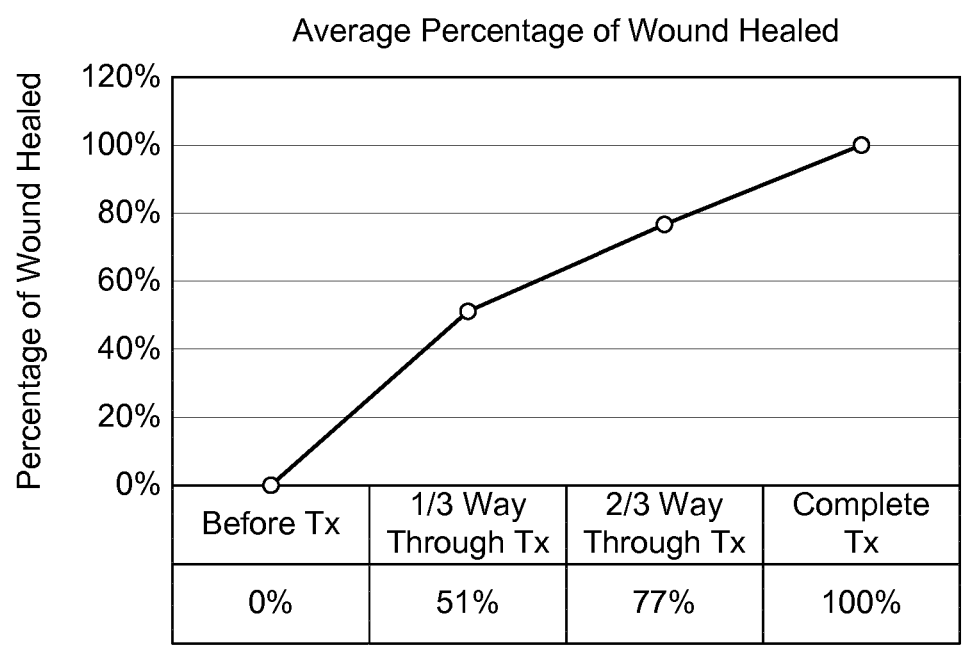
FIG. 13 illustrates a plot of wound healing in subjects following application of AM and FM modulations in repetition in accordance with one embodiment of the present invention.

One example of wound rehabilitation frequency composition is as follows:
AM Modulation:
7.83 Hz for 10 seconds
22 Hz for 10 seconds
108 Hz for 5 seconds
25 Hz for 10 seconds
190 Hz for 10 seconds
27 Hz for 10 seconds
10 Hz for 10 seconds
220 Hz for 10 seconds
27 Hz for 10 seconds
727 Hz for 5 seconds
787 Hz for 5 seconds
880 Hz for 5 seconds
22 Hz for 5 seconds
500 Hz for 10 seconds
2720 Hz for 5 seconds
3000 Hz for 5 seconds
27 Hz for 5 seconds
5000 Hz for 5 seconds
22 Hz for 5 seconds
10000 Hz for 5 seconds
then repeat In this Example, the FM modulation applies a three chord combination at the same time, as follows.
Signal 1
174 Hz for 10 seconds
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
then repeat
Signal 2
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
then repeat
Signal 3
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
285 Hz for 10 seconds
then repeat Three patients were treated every other day for 4 to 6 weeks using this composition. Results show epithelialization over 3 months, as shown in FIG. 13.

Bone Repair (2T3-Jax3)

In one embodiment the or each applicator 103 is placed over an area of bone injury or a post-surgical repair site and a composition applied for a predetermined period, for example, from about 20 minutes to about 30 minutes, at periodic intervals, for example, every other day or once weekly, over a period, for example, from about 4 weeks to about 6 weeks.

In one embodiment waves of different shape are applied, for example, triangular and square waves.

In one embodiment triangular waves having a frequency in the range of from about 31 Hz to about 39 Hz are applied in combination with square waves having a frequency of from about 108 Hz to about 500 Hz in order to promote bone healing and mitigate edema, and from about 10000 Hz to about 50000 Hz in order to provide pain relief.

Example (Jax3)

One example of bone repair composition is as follows:
AM Modulation:
3 Hz for 5 seconds
7.82 Hz for 10 seconds
31.2 Hz triangle wave for 10 seconds
108 Hz for 10 seconds
33 Hz triangle wave for 10 seconds
90 Hz for 10 seconds
108 Hz for 10 seconds
27 Hz for 10 seconds
10 Hz for 10 seconds
108 Hz for 10 seconds
34 Hz triangle wave for 10 seconds
500 Hz for 10 seconds
33 Hz for 5 seconds
880 Hz for 5 seconds
33 Hz triangle wave for 10 seconds
1577 Hz for 5 seconds
10 Hz for 10 seconds
3000 Hz for 5 seconds
33 Hz triangle wave for 10 seconds
5000 Hz for 5 seconds
31.2 Hz triangle wave for 10 seconds
13000 Hz for 10 seconds
then repeat from 7.82 Hz In this Example, the FM modulation applies a three chord combination at the same time, as follows.
Signal 1
174 Hz for 10 seconds
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
then repeat
Signal 2
285 Hz for 10 seconds
396 Hz for 10 seconds
417 Hz for 10 seconds
528 Hz for 10 seconds
639 Hz for 10 seconds
741 Hz for 10 seconds 852 Hz for 10 seconds
963 Hz for 10 seconds
174 Hz for 10 seconds
then repeat
Signal 3
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
285 Hz for 10 seconds
then repeat Example In this Example, fractures in pediatric patients were studied with hyperthermia treatment using the above composition (N=6) and without hyperthermia treatment (N=5).

Figure 14:
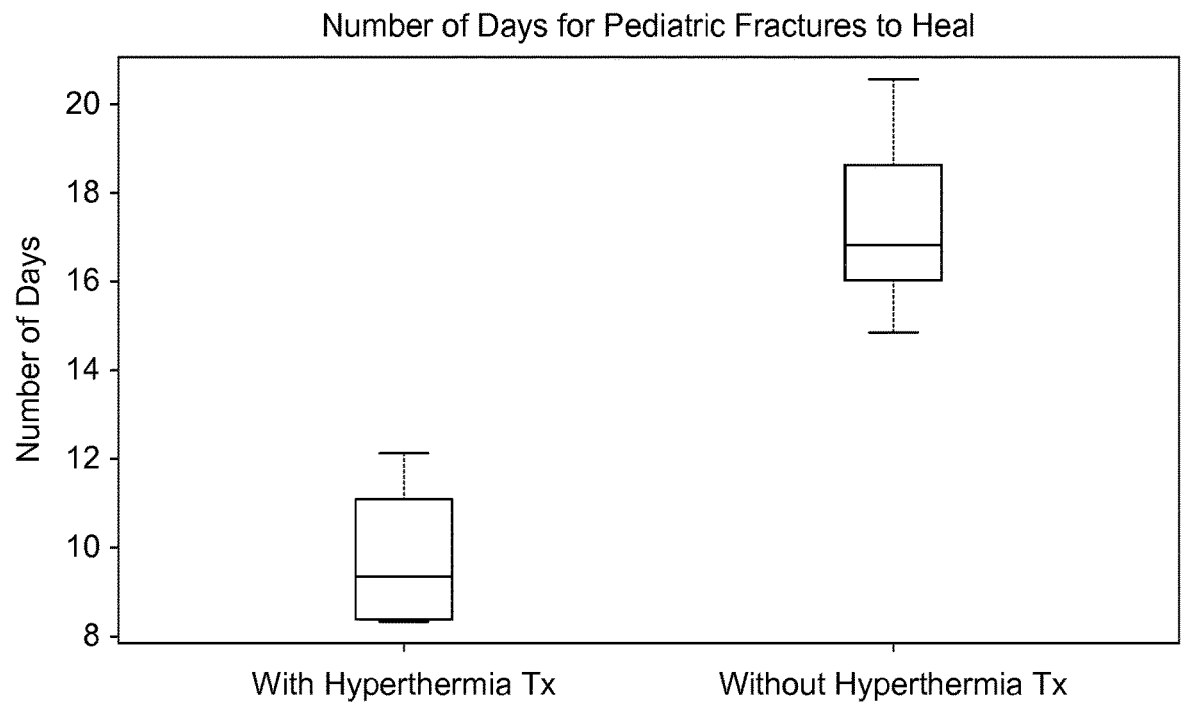
FIG. 14 illustrates a plot of healing of bone fractures in pediatric subjects following application of AM and FM modulations in repetition in accordance with one embodiment of the present invention.

As will be seen from FIG. 14, repair of pediatric fractures occurred in two weeks by stimulating the fracture site twice weekly for two weeks.

Example

In this Example, fractures in adult patients were studied with hyperthermia treatment using the above composition (N=6) and without hyperthermia treatment (N=6).

Figure 15:
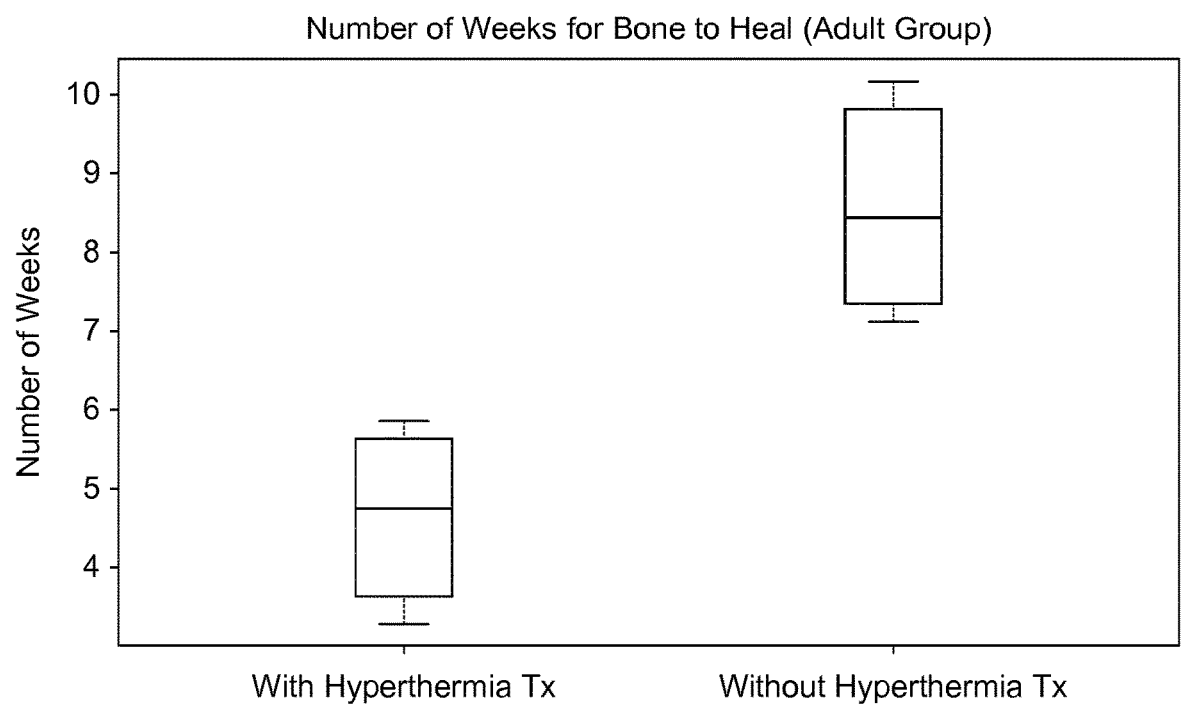
FIG. 15 illustrates a plot of healing of bone fractures in adult subjects following application of AM and FM modulations in repetition in accordance with one embodiment of the present invention.

The patients were treated once or twice a week. As shown in FIG. 15, swelling was reduced by 50% on average after 30 minutes of treatment. A numeric pain score of 1 to 10 was also recorded before and after full treatent. The average decrease in pain scores for patients with the hyperthermia treatment was 7, while the average decrease in pain scores for those patients without the hyperthermia treatment was 4.

Stone/Calcification Removal (Bam4-2T4)

In one embodiment the apparatus can be employed to shatter, vibrate and dissolve unwanted biological calcifications in tissues non-invasively in vivo, and in particular the non-invasive dissolution of calcific tendinopathy, gall bladder stones, kidney stones, ureteral stones, bladder stones, urethral stones, pancreatic duct stones, sialoliths (salivary duct stones), other stones or calcifications stuck in a duct of the body.

In one embodiment the composition is applied periodically, for example, every day or every other day, for a period, for example, from about 30 minutes to about 60 minutes, over the unwanted calcification for a period of time, for example, from about 1 week to about 4 weeks until resolution of the unwanted calcification. The extent of dissolution of calcifications can be monitored with x-ray or ultrasound imaging.

Example

Figure 16:
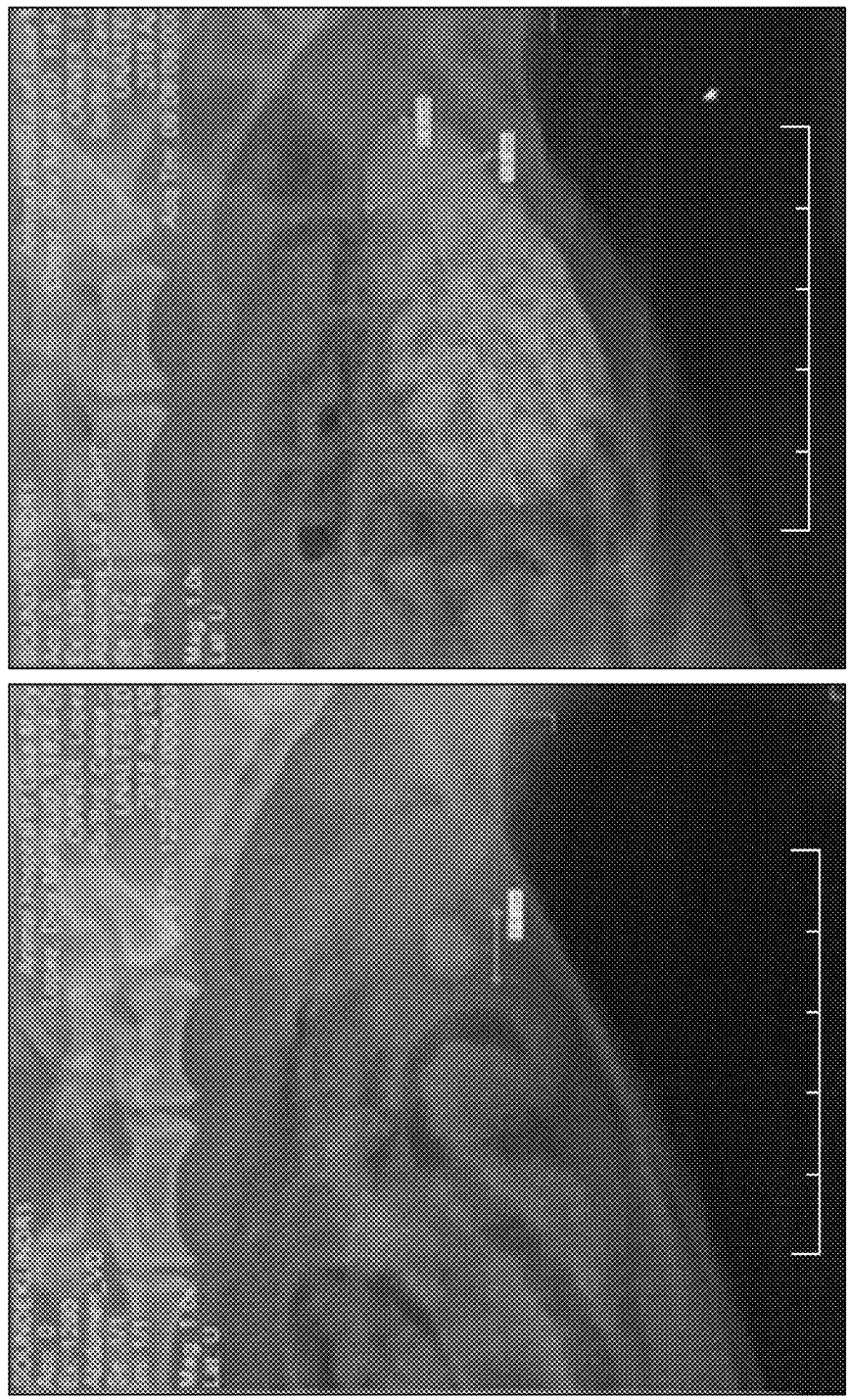
FIG. 16 illustrates images of the dissolution of bladder stones in a subject following application of AM and FM modulations in repetition in accordance with one embodiment of the present invention.

A canine with a bladder full of struvite bladder stones was treated with the above composition, and following treatment dissolution of all but one stone occurred, as shown in FIG. 16.

Treatment was applied for 30 to 60 minutes, three times a week over a three-month period to dissolve the stones.

Example

A feline was presented with 11 stones in ureter of about 2 mm to 3 mm in diameter.

Figure 17:
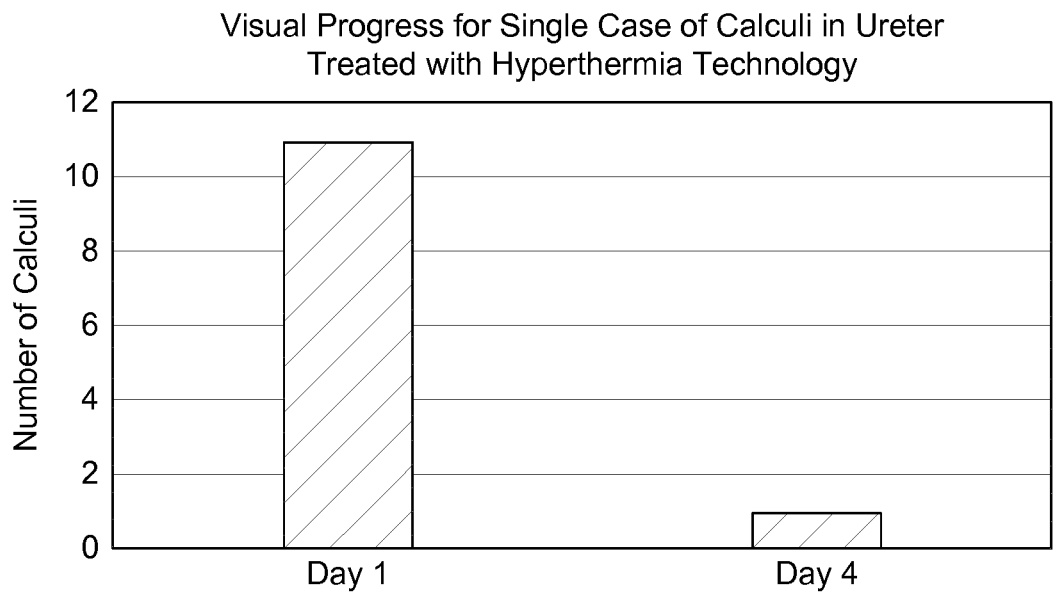
FIG. 17 illustrates a plot of visual progress scores in the dissolution of bladder stones in the subject of FIG. 16.

The feline was given 1 hour of hyperthermia treatment over kidneys and abdomen using the above composition set for 3 days. On the fourth day, a repeat ultrasound showed only 1 stone was left, as shown in FIG. 17. Treatments were repeated twice a week for 1 month. It was also noted that the patient went from renal failure to normal.

Example

A sample of 3 cats and 5 dogs with stones were treated with the hyperthermia using the above composition set.

The patients treated for small stones (between 3 mm and 10 mm) were treated twice a week for a month. The patients with larger stones or a large number of stones were treated twice a week for 5 to 6 months.

Figure 18:
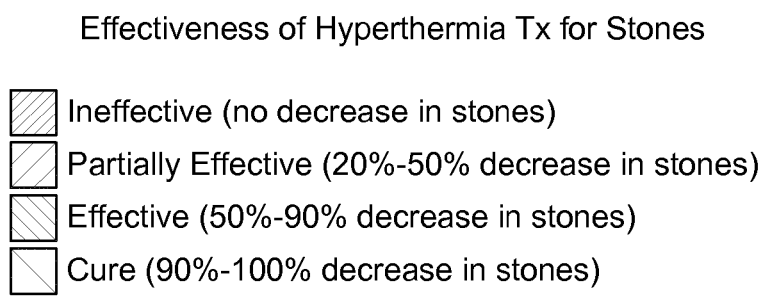
FIG. 18 illustrates a plot of effectiveness scores in treating body stones in subjects following application of AM and FM modulations in repetition in accordance with one embodiment of the present invention.
Figure 18:
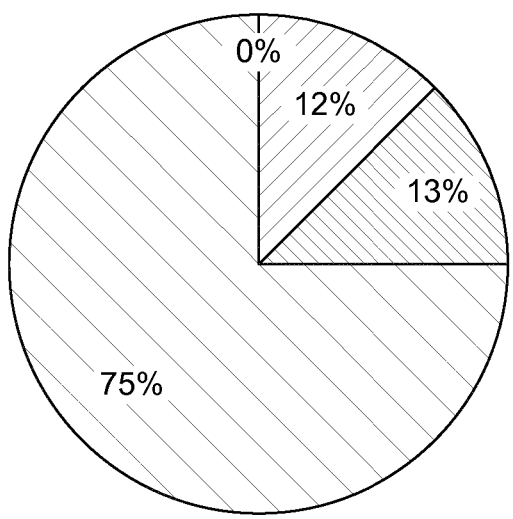

After final treatment, as shown in FIG. 18, the treatment was either ineffective (no decrease in stones), partially effective (20%-50% decrease in stones), effective (50%-90% decrease in stones), or cure (90%-100% decrease in stones).

Arthritic Rehabilitation (Shan4)

The apparatus can be employed to dissolve and warm unwanted arthritic calcifications in joints of the body and to help regain a normal range of motion when the body is pre-treated with the apparatus and then subjected to rehabilitative stretching.

In one embodiment the or each applicator 103 is placed over the desired joint while delivering the unwanted calcification dissolving frequency set for a period of time, for example, about 30 minutes, and then the joint is stretched and flexed with a variety of physical therapy stretching techniques in order to break past areas of restriction with the stretching exercises while the joint is warm and oscillating. In one preferred embodiment treatment of affected joints is periodically, for example, every other day, for a period, for example, 30 minutes, each for a period, for example, four weeks, followed by immediate stretching and range of motion exercises right after each oscillatory treatment.

Example (Shan4)

One example of calcification dissolution composition is as follows:
AM Modulation:
7.82 Hz for 10 seconds
16 Hz for 10 seconds
34 Hz for 10 seconds
16 Hz for 10 seconds
55 Hz for 10 seconds
16 Hz for 10 seconds
108 Hz for 10 seconds
13000 Hz for 10 seconds
16 Hz for 10 seconds
1000 Hz for 5 seconds
16 Hz for 10 seconds
2000 Hz for 5 seconds
16 Hz for 10 seconds
3000 Hz for 5 seconds
16 Hz for 10 seconds
5000 Hz for 5 seconds
16 Hz for 10 seconds 10000 Hz for 3 seconds
3 Hz for 5 seconds
then repeat In this Example, the FM modulation applies a three chord combination at the same time, as follows.

Signal 1
174 Hz for 10 seconds
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
then repeat Signal 2
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
then repeat Signal 3
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
285 Hz for 10 seconds
then repeat Example A 53 year old man with a history of knee injury 35 years ago, re-injured his knee and presented with swelling above and around the knee cap, 90 percent range of motion without pain and a pain level of 7 out of ten on presentation.

The knee was treated with the above composition set of frequencies (Shan4) for 30 minutes with a target temperature of 39° C. Immediately after the therapy, the swelling was reduced by 60 percent, and, on a pain score scale of 10 (0 being no pain), the pain score was 2 and the range of motion was back to 100 percent.

The therapy was repeated two days later and all of the swelling was gone, motion was at a 100 percent range of motion, and the pain score was 0.

The effects of the treatment continued at one and two month follow-ups, with a pain score of 0, and a range of motion of 100%.

Example

A patient was given injectable Polyglycan, a combination of hyaluronic acid, chondroitin 4 and 6 and glucosamine, once to twice weekly for four to six weeks, and the area of interest was energized with the applicator 103 employing a composition set of anti-inflammatory, analgesic collagen regenerative frequencies over the desired joints to be treated at between 37° C. and 41° C., in order to change the phase of the GAGs (glycosaminoglycans) and the water cartilage interphase at the joint surface.

This treatment is postulated to promote reassembly of a thicker EZ Water and GAG electronegative surface along the joint surface area by promoting a thicker EZ water layer over the joint surface. The charging up of these apposing electronegative joint surfaces increases joint spaces and promotes joint homeostasis. In this embodiment the device is used to enhance a phase transition on the joint surfaces of $H_2O$ into $H_3O_2$ through a non-invasive dielectric coupling method. This is a particularly effective way to increase electronegativity along a joint surface in a non-invasive way for the treatment of joint inflammation and pain.

Magnetophoresis

In one embodiment the apparatus facilitates the removal into extracellular fluid for excretion of excess magnetite ($Fe_3O_4$), which arises from magnetite crystals from tau proteins in brain microtubules, and other heavy metals from neurologic tissue as found in senile plaques and Alzheimer's disease. The apparatus plays standing waves in a composition that are capable to oscillate the nanoparticles.

Nano-Oscillation Debris Removal (LiI5).

The apparatus can be employed to stir and agitate the intracellular microtubules and water interface, and facilitate removal of intracellular debris and other mediators of intracellular inflammation and toxins, as intracellular edema, out of the cells. The vibration caused by the various standing wave frequencies in the cells assist in the vibratory removal of intracellular debris into the extracellular environment for efficient removal of this debris out of the cells and out of the body.

The oscillation of the water-micro-tubular-cell interface with standing waves of various frequencies created by radio frequency energy of various AM and FM modulations, in particular triplet FM modulations, are used to impart potential energy into the water by means of ionic cyclotron energy, and this gives the water under the influence of the at least one applicator 103 the energy to separate charges into positive and negative charges along hydrophilic surfaces and to create ordered structured water along the same hydrophilic surfaces.

The creation of strong stimulating standing waves by the apparatus by variable AM and FM modulated carrier signals imparted into tissues, in particular with a left handed metamaterial lens applicator, allows an efficient means to stimulate tissues and organs under the at least one applicator 103 with oscillating standing waves capable of removing intracellular debris, toxins and cellular mediators of inflammation out of the cells and nerve cells and axons into the extracellular environment for removal. A thixotropic effect enhanced by magnetophoresis enhances the removal of cellular toxins and mediators of inflammation.

The oscillations created in the tissues by the standing waves created by the apparatus offer a non-invasive means to remove intracellular toxins, debris and intracellular mediators of inflammation from inside the cells under the energy delivered by the at least one applicator 103 and the oscillations facilitate the removal of intracellular debris into the extracellular milieu for facilitated excretion.

Slower peristaltic AM modulations are alternated with faster intracellular thixotropic oscillations in order to facilitate extracellular pumping of recently excreted/oscillated material from inside of the cell away from the targeted oscillated area for removal.

Example (LiI5)

One example of intracellular debris removal composition is as follows:
AM Modulation:
7.82 Hz for 10 seconds
16 Hz for 10 seconds
1.25 Hz for 10 seconds
55 Hz for 10 seconds
1.25 Hz for 10 seconds
16 Hz for 10 seconds
1.25 Hz for 10 seconds
55 Hz for 10 seconds
1.25 Hz for 10 seconds
16 Hz for 10 seconds
1000 Hz for 5 seconds
16 Hz for 10 seconds
2000 Hz for 5 seconds
16 Hz for 10 seconds
3000 Hz for 5 seconds
16 Hz for 10 seconds
5000 Hz for 5 seconds
16 Hz for 10 seconds
10000 Hz for 5 seconds
1 MHz for 5 seconds
2 MHz for 5 seconds
then repeat In this Example, the FM modulation applies a three chord combination at the same time, as follows.
Signal 1
174 Hz for 10 seconds
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
then repeat
Signal 2
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
then repeat
Signal 3
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
285 Hz for 10 seconds
then repeat Respiratory The apparatus can be employed to loosen and break up phlegm in lungs and bronchial and tracheal passages.

In one embodiment this composition is used to provide rapid relief of respiratory symptoms by placing the at least one applicator 103 on the dorsal and ventral/cranial and caudal chest wall over the lungs and bronchial bifurcations as species specific for a period of time, for example, from about 15 minutes to about 30 minutes, with a target temperature of from about 37° C. to about 41° C.

Example

Twenty human and animal patients were presented with signs of asthma and pneumonia, such as kennel cough, respiratory distress, and difficulty breathing along with nasal discharge.

Figure 19:
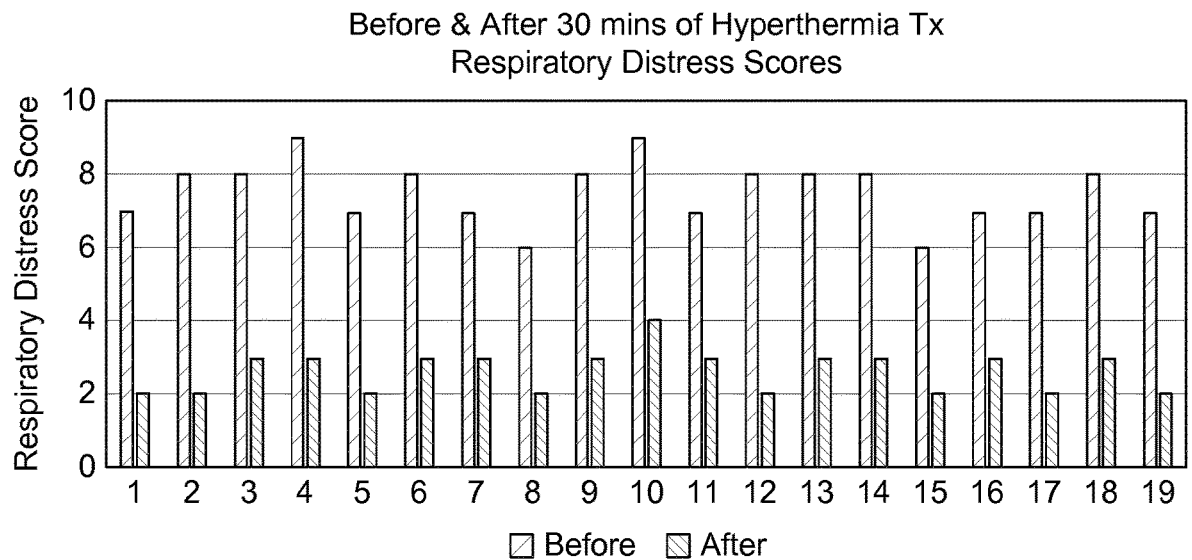
FIG. 19 illustrates a plot of respiratory distress scores in subjects following application of AM and FM modulations in repetition in accordance with one embodiment of the present invention.

Each patient was scored before and after treatment for 30 minutes on a scale of 1 (normal) to 10 (worst case) based on such signs and respiratory effort. As will be seen in FIG. 19, rapid relief of respiratory symptoms as measured by decreased respiratory effort and expectoration of mucous was observed immediately after the therapy.

Circulatory System Support (Pop6-2T6)

The apparatus can be employed to improve local circulation through the generation of rhythmic AM and FM modulated standing waves that propagate a peristalsis-like wave through tissues in order to facilitate the acceleration of fluid movement through the tissue under the or each applicator 103.

The standing wave nanooscillation of cardiac tissue by the apparatus and the standing wave set of cardiac supporting frequencies may be used as a way to deliver increased blood flow and oxygenation to cardiac tissue, induce HSP production and nanothixotropic stimulation of cardiac tissue, and to support nanofluid dynamics in cardiac tissue.

In one embodiment the composition set of frequencies can be employed to facilitate a 75 bpm pulse rate, with an approximately 1.25 Hz rhythm under the or each applicator 103.

In another embodiment a pulse rate monitor provides active feedback of the patient's heart/pulse rate, and the apparatus matches the monitored heart rate as the rhythm employed by the cardiac/circulatory mode of the apparatus. If no active feedback is given by the heart rate monitor, then a 75 beat per minute pulse is delivered as the default.

The apparatus can also promote the production of HSPs, including hsp70, hsp90 and hsp27, in cardiac tissue by applying the circulatory set of frequencies as above over the heart or other vessels selected and energized under the or each applicator 103.

Example

One example of cardiac circulation composition is as follows:
AM Modulation:
7.82 Hz for 10 seconds
1.25 Hz for 10 seconds
16 Hz for 5 seconds
1.25 Hz for 10 seconds
55 Hz for 5 seconds
1.25 Hz for 10 seconds
7.82 Hz for 10 seconds
1.25 Hz for 10 seconds
16 Hz for 10 seconds, then repeat one or more times from 7.82 Hz
3000 Hz for 5 seconds
16 Hz for 10 seconds
5000 Hz for 5 seconds
1.25 Hz for 10 seconds
10000 Hz for 5 seconds 16 Hz for 10 seconds
5000 Hz for 5 seconds
16 Hz for 10 seconds
1000 Hz for 5 seconds In this Example, the FM modulation applies a three chord combination at the same time, as follows.

Signal 1
174 Hz for 10 seconds
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
then repeat Signal 2
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
then Signal 3
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
285 Hz for 10 seconds
then repeat Example 5 patients were treated with the above composition set over the heart and hilar lymph nodes to support heart function through vasodilation and HSP formation, with no ill effects three months post follow-up. Bronchodilation and decrease of pulmonary edema are a noted effect visible immediately after therapy from x-ray imaging.

Organ Transplant Pre-Implant Readiness

The viability of tissues to be transplanted can profit from pre-conditioning by enhancing the synthesis of HSPs with the use of the apparatus.

A problem in the field of transplant medicine is the delicate balance of preparing and transporting organ transplants from donors so that organs can be viable for transplant, especially in cases of a prolonged time between organ collection and transplant. This is particularly relevant in the case of lung transplants.

In this embodiment the apparatus comprises a chilled, oxygenated, ozonized, fluid media transport chamber, which includes or is lined with a plurality of applicators, typically from two to four applicators 103, in order to impart energy into the chilled fluid environment.

Where no transportation is necessary, the unit may be used as a pre-implant treatment receptacle/vessel for the preparation of the organ, typically a lung sample.

The organ can be maintained chilled but energized, for example, by employing at 50% duty cycle, with a composition of frequencies intended to mimic physiologic micro tubular and mitochondrial vibrations into the media during transport in order to optimize the organ sample, in order to nanooscillate the microtubules in the chilled oxygenated media.

After transport, the organ can be "thawed" by the same device by simply removing or switching off the cooling mechanism. A cooled oxygen and ozone enriched media surrounds the organ during energized transport or standard liquid helium transport in the case of kidneys.

The above-described scheme allows for thixotropic liquefaction of the intercellular milieu in order to optimize organ viability prior to implantation.

The device can be miniaturized and attached to the container or table side ready chamber, and powered by a battery pack or external power supply during transport.

Anti-bacterial anti-fungal and anti-viral resonances can be energized in the oxygenated physiologic fluid milieu bathing the organs in order to help eliminate unwanted pathogens in recipient organs through use of a scheme where organs are preheated and stimulated with anti-pathogenic resonant frequencies.

In one embodiment the device can be used to energize an organ while frozen and transported, and then used to thaw the same organ when the time for implantation and thawing occurs. This device may be placed under the organs while in a cooler or freezer, such as by using TMS bulkhead RF connectors into the cooler/freezer to allow energizing of the sample.

Example

One example of storage and transport composition is as follows:

AM Modulation:
7.82 Hz for 10 seconds
16 Hz for 10 seconds
1.25 Hz for 10 seconds
55 Hz for 10 seconds
10,000 Hz for 10 seconds
444 Hz for 3 seconds
2008 Hz for 10 seconds
1.25 Hz for 10 seconds
3000 Hz for 10 seconds
3 Hz for 10 seconds
5000 Hz for 5 seconds
333 Hz for 3 seconds
then repeat FM Modulation:
10000 Hz for 5 seconds
2720 Hz for 5 seconds
727 Hz for 3 seconds
880 Hz for 3 seconds
787 Hz for 3 seconds
393000 Hz for 3 seconds
220 Hz for 3 seconds
1.25 Hz for 3 seconds
1823 Hz for 3 seconds
then repeat The apparatus can also be used to decrease edema of lungs and other organs for transplant preparation.

In one embodiment the apparatus is used to stimulate the fluid around organs in a bath for preparation prior to transplant in order to reduce edema of tissues being prepared for transplant.

In one embodiment the or each applicator 103 can be dressed in a sterile disposable plastic applicator cover and submerged in the bathing physiological solution in order to energize the desired tissue as an electronic anti-inflammatory for organ transplant edema.

In one embodiment a water-soluble colloid gel can be mixed with a formulation of radio coupling enhancing minerals selected from at least one of 1-5% concentration of quartz, 1-5% concentration of amethyst, 1-5% concentration of emerald, 1-5% concentration of sapphire, 1-5% concentration of zeolite/clinoptilolite, 1-5% concentration of hematite, 1-5% concentration of snowflake obsidian, 1-5% concentration of magnetite, 1-5% concentration of supraparamagnetic iron oxide nanoparticles (SPIONs).

In one embodiment the radio enhancing minerals can comprise metamaterial supraparamagnetic iron oxide nanoparticulate ferro fluid composition of 30 mg/ml concentration, being a mixture of 20 mg/ml of 30 nm SPION and 8 mg/ml of 10 nm SPION and 2 mg/ml of 5 nm SPION.

In one embodiment the apparatus can be energized over the target area with a frequency composition of from about 44 Hz to about 500 Hz and from about 200 KHz to about 600 KHz, in order to maximize the resonant maximum vibratory rate of the SPION mixture at the target site under the or each applicator 103.

Example 25 dogs were treated with the hyperthermia treatment using the above composition set once a week for 4 weeks along with heart medication.

Figure 20:
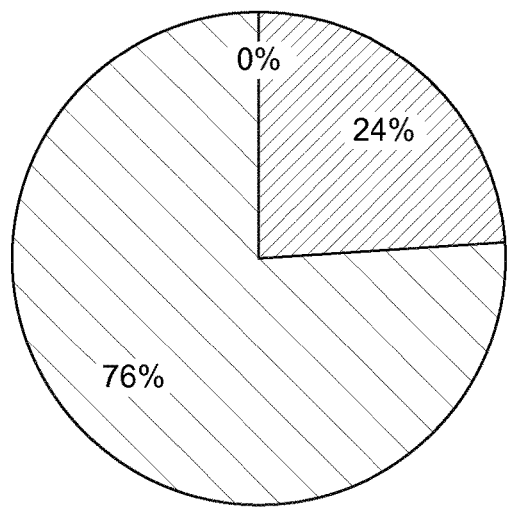
FIG. 20 illustrates a plot of effectiveness scores in cardiac and circulatory improvement in subjects following application of AM and FM modulations in repetition in accordance with one embodiment of the present invention.

After 4 weeks, it was noted if the patients's respiratory effort increased, and exercise and effort to be active increased. Based on these measures, it was noted if each patient showed no improvement, moderate improvement, or major improvement. These results are shown in FIG. 20.

Inflammatory Bowel Disease, Crohn's Disease (Pop6-2T6)

The apparatus can be used to promote the production of HSPs, including hsp70 and hsp90, in intestinal tissue, including the stomach, the small intestine and the large intestine, by applying the circulatory set of frequencies.

hsp70 production in the intestine promotes the propagation of beneficial gut flora and is detrimental for unwanted intestinal flora.

Example 5 cats and dogs were treated for Crohn's disease twice a week for 2 to 3 weeks.

Before and after treatment, disease activity indexes (0-21) were recorded. The disease activity index scoring system is shown below in Table 1.

TABLE 1

| Disease Activity | Score |
|---|---|
| Diarrhea (number of daily stools) | |
| 0-2 | 0 |
| 3-4 | 1 |
| 5-6 | 2 |
| 7-9 | 3 |
| >10 | 4 |
| Nocturnal diarrhea | |
| No | 0 |
| Yes | 1 |

TABLE 1-continued

| Disease Activity | Score |
|---|---|
| Visible blood in stool (% of BM) | |
| 0% | 0 |
| <50% | 1 |
| >50% | 2 |
| 100% | 3 |
| Fecal incontinence | |
| No | 0 |
| Yes | 1 |
| Abdominal pain | |
| None | 0 |
| Mild | 1 |
| Moderate | 2 |
| Severe | 3 |
| General well-being | |
| Perfect | 0 |
| Very Good | 1 |
| Good | 2 |
| Average | 3 |
| Poor | 4 |
| Terrible | 5 |
| Abdominal tenderness | |
| None | 0 |
| Mild and localized | 1 |
| Mild to moderate and diffuse | 2 |
| Severe or rebound | 3 |
| Need for anti-diarrheals | |
| No | 0 |
| Yes | 1 |

Figure 21:
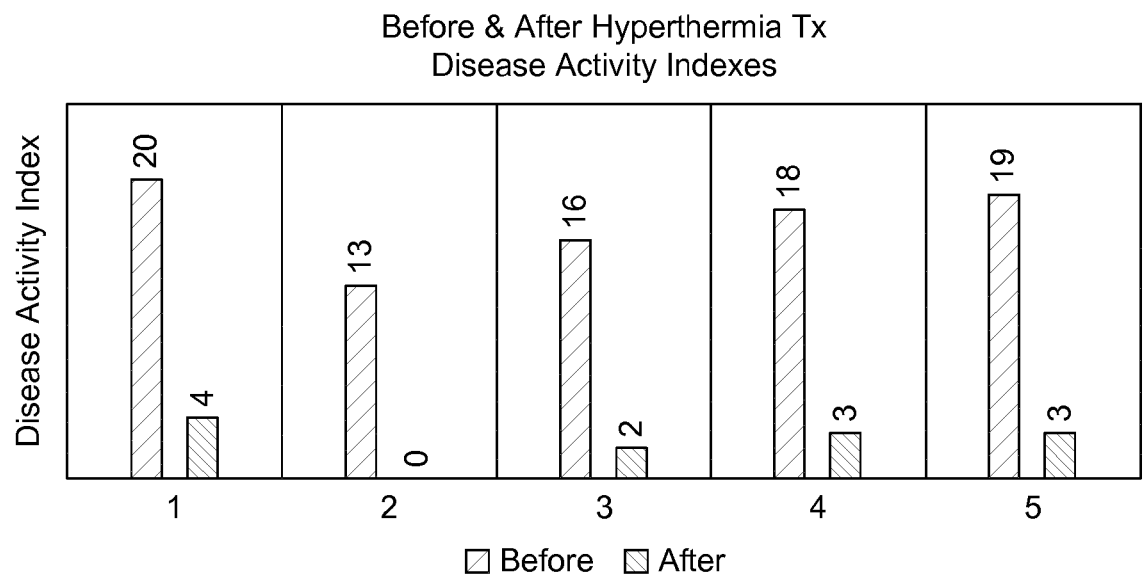
FIG. 21 illustrates a plot of disease activity index (CDAI) in subjects suffering from Crohn's disease following application of AM and FM modulations in repetition in accordance with one embodiment of the present invention.

As will be seen from FIG. 21, a significant improvement on average was seen following treatment.

Hyperthermia Through Low-Power Resonant Standing Wave Modulation

The apparatus can be employed to create standing waves in tissue that increase the local temperature under the applicator 103 for the precise control of temperature locally, with considerably lower power as compared to conventional microwave hyperthermia units that require with a water bolus to cool off the skin, by the efficient use of local resonant frequencies in tissues being energized and oscillated by the apparatus, and an efficient back plane on a modified z strip patch meta-material applicator.

In one embodiment the apparatus creates standing waves that increase the heat of friction of water and the microtubules under the direct contact of the or each applicator 103 to a variable depth range of from about 4 cm to about 15 cm depending on tissue and material treated.

AM and FM modulation of the carrier signals allows the temperature of the energized tissues to be raised in a controlled homogenous fashion that lends itself well to local hyperthermia of biological tissues with a wide margin of safety.

Cancer Killing Resonances (Mia7)

The apparatus can be employed to enhance apoptosis of neoplastic cells by matching the resonant frequency of those neoplastic cells, and one or more of increasing the local temperature of the tumor, increasing the local pH, increasing local oxygen delivery to the tumor, increasing mitochondrial damage of tumor cells, increasing intra-tumor production of tissue necrotic factor alpha, activating the immune system against the tumor through the production of TNF alpha and hsp70, and promoting free radical damage inside the tumor.

The apparatus can also be employed to facilitate the presentation of oscillated and heated tumor parts to the dendritic cells, and stimulate an immune response with the purpose of creating an in vivo cancer vaccine that specifically targets the tumor being warmed and oscillated under the or each applicator 103.

The apparatus can also be used in combination with supraparamagnetic iron oxide nanoparticles (SPIONs), gold nanoshell supraparamagnetic iron oxide nanoparticles (gold SPIONs), chemotherapeutic drugs, such as carboplatin, cisplatin, 2-desoxy-D-glucose, dl-glycerol-aldehyde, immune therapy and glucose metabolic inhibitors, in order to further increase metabolic stress inside the tumors and enhance an activated immune response against the tumor in vivo.

In one embodiment the composition set can include frequencies which reduce cancer breakthrough pain by oscillating out chemical mediators of inflammation from around pain receptors surrounding the tumor and by providing pain mitigating frequency compositions that include pain blocking frequencies, for example, frequencies in the range of from about 10000 Hz to about 50000 Hz.

Example

One example of cancer killing composition is as follows:
AM Modulation:
7.82 Hz for 10 seconds
16 Hz for 10 seconds
1.25 Hz for 10 seconds
55 Hz for 10 seconds
10,000 Hz for 10 seconds
16 Hz for 10 seconds
2008 Hz for 10 seconds
1.25 Hz for 10 seconds
3000 Hz for 10 seconds
16 Hz for 10 seconds
5000 Hz for 5 seconds
16 Hz for 10 seconds
10000 Hz for 5 seconds
then repeat
In this Example, the FM modulation applies a three chord combination at the same time, as follows.
Signal 1
174 Hz for 10 seconds
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
then repeat
Signal 2
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
then repeat
Signal 3
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
285 Hz for 10 seconds
then repeat This set of frequencies is effective to facilitate the removal of intracellular debris and promote apoptosis of bacteria, viruses, fungi and neoplastic cells, and, when used in combination with supraparamagnetic iron oxide solutions (SPIONs), as a way to inactivate various bacterial and fungal biofilms and as a method to enhance heating of infected tissues.

Osteogenic Stem Cells (Mom8)

The apparatus can be employed to stimulate cell propagation and support stem cell activation and differentiation in tissues, in combination with stimulating the production of hsp70.

This set of frequencies promotes strong bones to counteract osteoporosis and decreases fat deposition under the local areas treated.

Example

One example of a composition set for the stimulation and differentiation of osteogenic stem cells and fat heating is as follows:
AM Modulation:
3 Hz for 3 seconds
10 Hz for 5 seconds
90 Hz for 3 seconds
7.83 Hz for 5 seconds
0.8 Hz for 3 seconds
90 Hz for 5 seconds
0.9 Hz for 3 seconds
3000 Hz for 5 seconds
33 Hz for 3 seconds
90 Hz for 5 seconds
5000 Hz for 3 seconds
90 Hz for 5 seconds
13000 Hz for 3 seconds
then repeat
In this Example, the FM modulation applies a three chord combination at the same time, as follows.
Signal 1
174 Hz for 10 seconds
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
then repeat
Signal 2
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds 963 Hz for 10 seconds
174 Hz for 10 seconds
then repeat
Signal 3
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
285 Hz for 10 seconds
then repeat Example 8 dogs were treated with arthritis in their spine or back. Stem cell therapy was performed by placing an applicator on the stomach for 30 minutes, and then on an area of arthritis once a week for 4 weeks.

Figure 22:
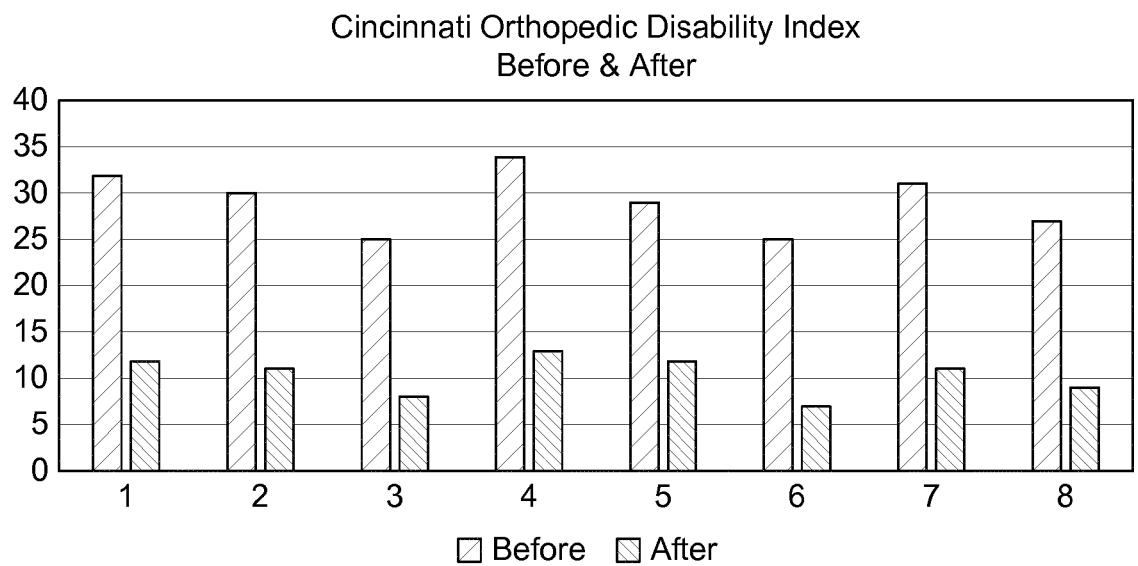
FIGS. 22 and 23 illustrate respectively plots of Cincinnati orthopedic disability index (CODI) and pain scores in subjects suffering from arthritis following application of AM and FM modulations in repetition in accordance with one embodiment of the present invention.
Figure 23:
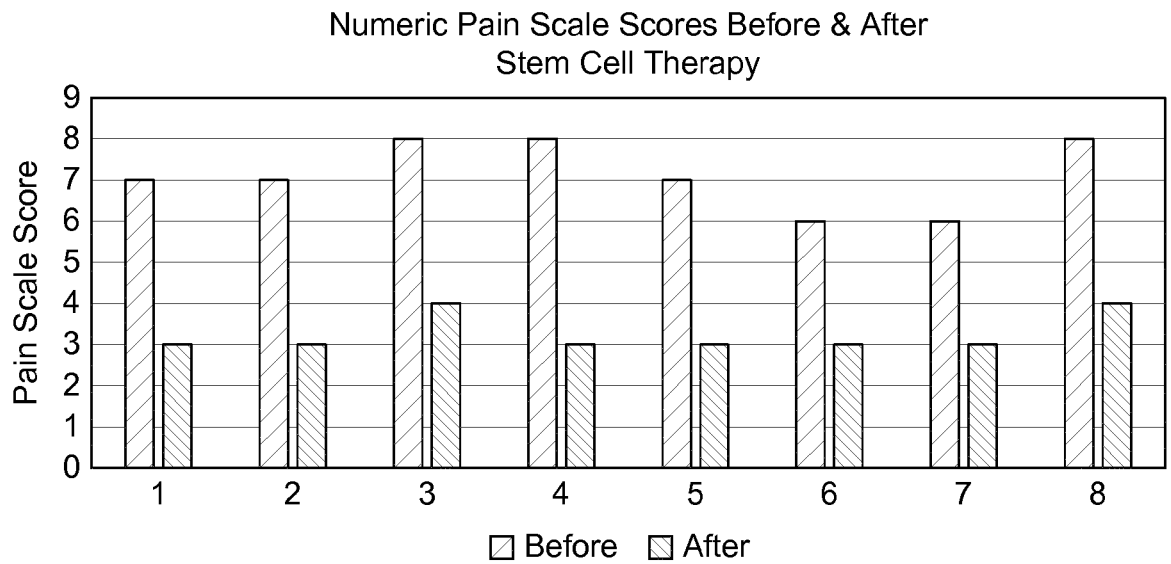

The Cincinnati Orthopedic Disability Index was taken before and after full treatment, as well as numeric 0-10 pain scale. As will be seen from FIGS. 22 and 23, a significant improvement is shown following treatment.

As will be seen, the present invention has particular application in treating Spinal intervertebral disc disease (IVDD).

Stem Cell Stimulation

The apparatus can be used for stem cell stimulation using an externally-applied applicator 103 on stem cell donor sites, including the falciform ligament and the sternum, ileac crest and femurs.

Example

A patient was treated for 30 minutes at a target temperature of about 37° C. using a composition of stimulatory and peristaltic-like resonant frequencies for the activation of the donor sites, and then subsequently a composition set of secretory rhythms were pulsated for 5 minutes at 1.25 Hz for 8 seconds and 3.0 Hz for 5 seconds, which is repeated for 5 minutes.

The overall hierarchical pattern of peristaltic-like distribution of the applied signals is applied to the applicators 103 with reference to the patient's orientation, such that the waves move from the donor site to the recipient site and is the stimulated at the recipient site for a defined period, typically from about 10 minutes to about 30 minutes per site after an initial period, typically 5 minutes, of peristaltic tractor waves moving towards the donor site.

Insulin Production (Falva 9)

The apparatus can be employed to stimulate insulin production and support hsp70 activation in pancreatic tissue in the presence of natural iron oxide or administered iron oxide nanoparticles.

Example

One example of an insulin production composition set is as follows:
AM Modulation:
3 Hz for 3 seconds
7.83 Hz for 10 seconds
10 Hz for 10 seconds
108 Hz for 5 seconds
5 Hz for 10 seconds
10000 Hz for 3 seconds
13 Hz for 10 seconds
10 Hz for 10 seconds
3 Hz for 5 seconds
5000 Hz for 3 seconds
7.83 Hz for 10 seconds
22 Hz for 10 seconds
108 Hz for 5 seconds
3000 Hz for 3 seconds
10 Hz for 10 seconds
3 Hz for 3 seconds
7.83 Hz for 10 seconds
13 Hz for 10 seconds
then repeat in a round In this Example, the FM modulation applies a three chord combination at the same time, as follows.
Signal 1
174 Hz for 10 seconds
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
then repeat
Signal 2
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
then repeat
Signal 3
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
285 Hz for 10 seconds
then repeat Example 4 cats began treatment with 8 units of insulin using the above composition set. The treatment involved heating the pancreas once a week for 4 weeks.

Figure 24:
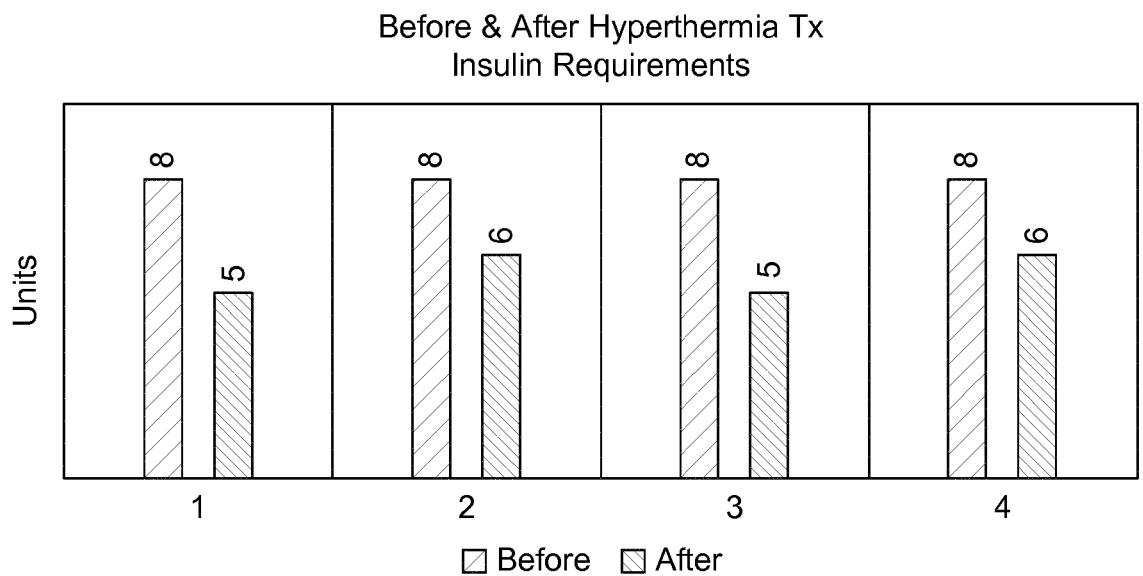
FIG. 24 illustrates a plot of insulin requirement in subjects following application of AM and FM modulations in repetition in accordance with one embodiment of the present invention.

A drop in insulin requirements was recorded, as shown in FIG. 24.

Musculo-Skeletal and Sport Injuries (Ez10)

The apparatus can be employed in the short-term management of musculo-skeletal and sport injuries.

This frequency set can stimulate repair processes, increase drug activity, allow more efficient relief from pain, help in the removal of toxic wastes, increase tendon extensibility and reduce muscle and joint stiffness. Hyperthermia induced vasodilation secondary to these specific standing waves induces hyperemia, improves local tissue drainage, increases metabolic rate and induces alterations in the cell membrane to facilitate the removal of lactic acid and other toxic wastes.

Example

One example of a musculo-skeletal composition set is as follows:
AM Modulation:
7.82 Hz for 10 seconds
10000 Hz for 5 seconds
16 Hz for 5 seconds
1.25 Hz for 3 seconds
3000 Hz for 5 seconds
16 Hz for 5 seconds
1.25 Hz for 10 seconds
55 Hz for 5 seconds
3 Hz for 10 seconds
5000 Hz for 5 seconds
1000 Hz for 5 seconds
7.82 Hz for 10 seconds
3 Hz for 10 seconds
16 Hz for 10 seconds, then repeat one or more times from 7.82 Hz
3000 Hz for 5 seconds
16 Hz for 10 seconds
5000 Hz for 5 seconds
1.25 Hz for 10 seconds
10000 Hz for 5 seconds
16 Hz for 10 seconds
5000 Hz for 5 seconds
16 Hz for 10 seconds
1000 Hz for 5 seconds
3 Hz for 10 seconds
then repeat in a round In this Example, the FM modulation applies a three chord combination at the same time, as follows.
Signal 1
174 Hz for 10 seconds
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
then repeat
Signal 2
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
then repeat
Signal 3
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
285 Hz for 10 seconds
then repeat Example 10 athletic dogs presented with sports injuries were treated with the above composiiton set once for 30 minutes. Numeric pain scales were recorded before and after the treatment; with 0 representing no pain and 10 representing worst possible pain.

Figure 25:
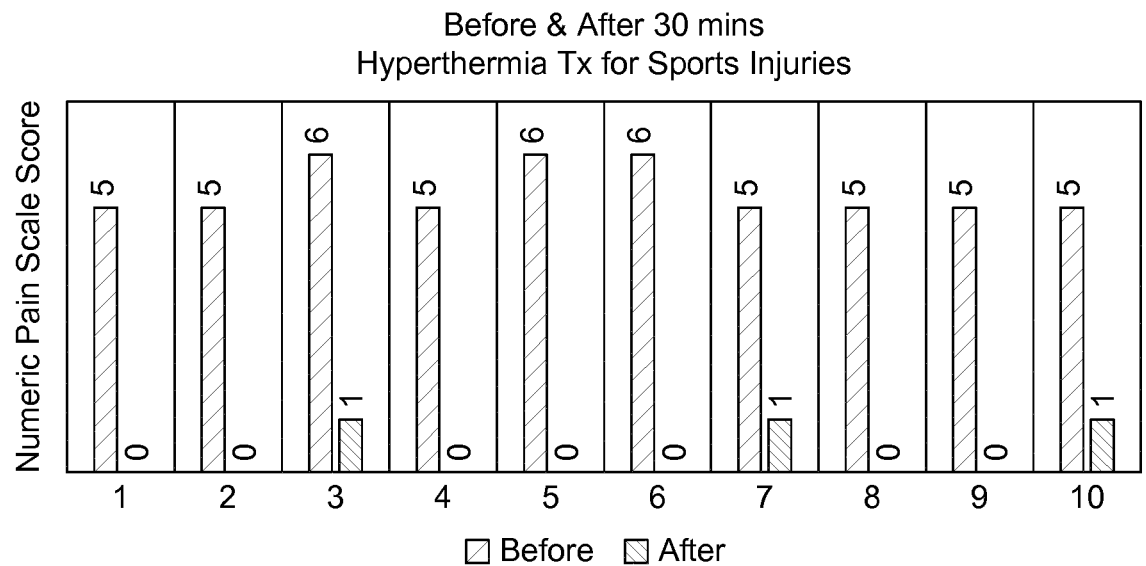
FIG. 25 illustrates a plot of pain scores in subjects suffering from sports injuries following application of AM and FM modulations in repetition in accordance with one embodiment of the present invention.

As will be seen from FIG. 25, the dogs show a marked improvement following treatment, with the majority having no pain.

Example 5 humans and 10 dogs were administered hyperthermia treatment using the above composition set for 10 to 15 mins on their major muscle groups.

Human patients noted that they felt more loose and that their energy increased. It was recorded whether patients felt more loose, appeared to have more energy, and saw an increase in overall muscle performance, with 90% of human patients feeling more loose and 100% seeing an increase in overall muscle performance, and 100% of dogs appearing to have more energy and increased muscle performance.

Example 3 humans and 7 dogs were given hyperthermia treatment using the above composition set for post conditioning.

Figure 26:
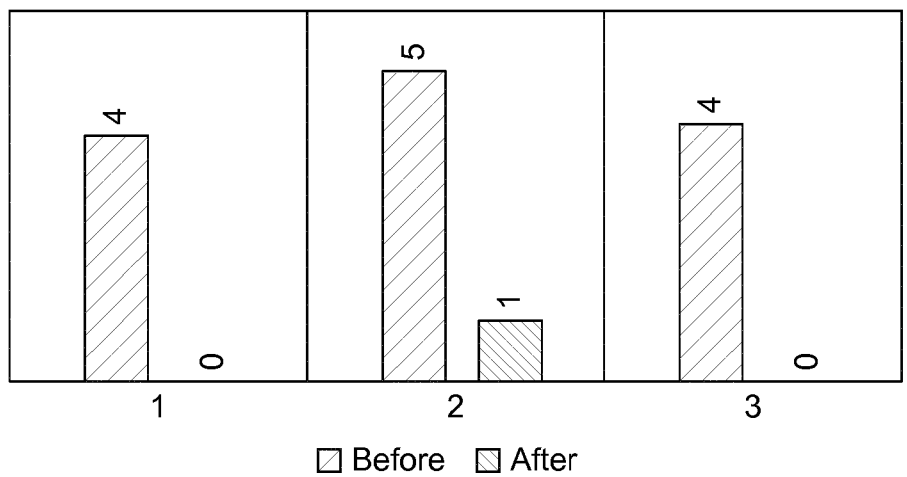
FIGS. 26 and 27 illustrate respectively plots of muscle soreness scores and pain scores in subjects suffering from muscular conditions following application of AM and FM modulations in repetition in accordance with one embodiment of the present invention.

A muscle soreness numeric score was recorded before treatment and the day after treatment for the human patients, with 0 representing no soreness and 10 representing extreme soreness. As will be seen from FIG. 26, a marked reduction in soreness was observed, with most having no soreness after treatment.

Figure 27:
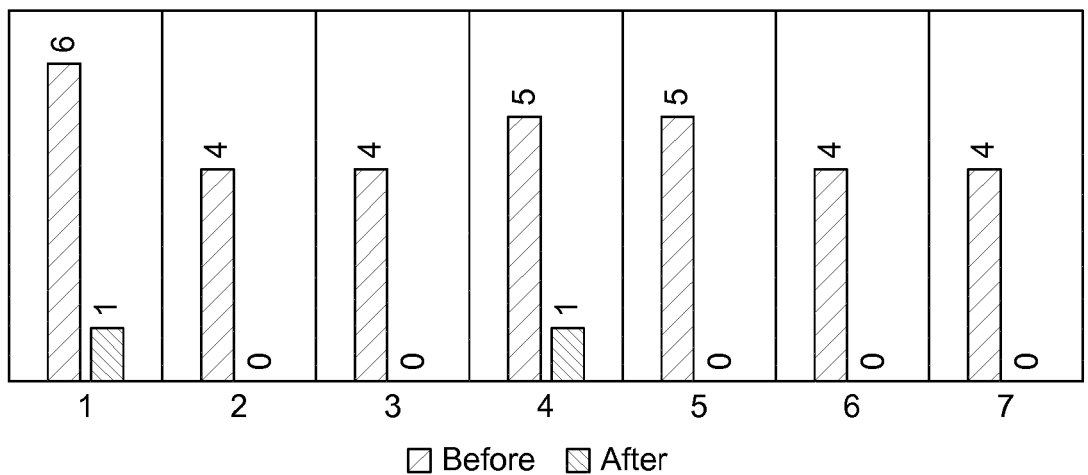

A numeric pain scale was recorded for the canine patients. As will be seen from FIG. 27, a marked reduction in pain was exhibited, with most having no pain after treatment.

Neuromuscular Disease (Mink 11)

The apparatus can be employed in the management of neuromuscular disease, including Parkinson's disease like tremors. The frequencies are designed to be neuro supportive.

Example

One example of a neuromuscular supportive composition set is as follows:
AM Modulation:
1.1 Hz for 5 seconds
95 Hz for 5 seconds
3.9 Hz for 5 seconds
169 Hz for 3 seconds
4334 Hz for 5 seconds
727 Hz for 10 seconds
1.1 Hz for 5 seconds
787 Hz for 10 seconds
10 Hz for 10 seconds
6000 Hz for 5 seconds
33 Hz for 5 seconds
7.82 Hz for 10 seconds
4334 Hz for 10 seconds
470 Hz for 10 seconds
10 Hz for 10 seconds 666 Hz for 5 seconds
3000 Hz for 5 seconds
1.25 Hz for 10 seconds
5000 Hz for 5 seconds
7.83 Hz for 10 seconds
10000 Hz for 5 seconds
16 Hz for 10 seconds
5000 Hz for 5 seconds
95 Hz for 10 seconds
470 Hz for 5 seconds
95 Hz for 10 seconds
then repeat in a round In this Example, the FM modulation applies a three chord combination at the same time, as follows.

Signal 1
174 Hz for 10 seconds
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
then repeat Signal 2
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
then repeat Signal 3
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
285 Hz for 10 seconds
then repeat Example 3 dogs were presented with tremors, and treated by placing an applicator on their head for 30 minutes using the above composition set.

Figure 28:
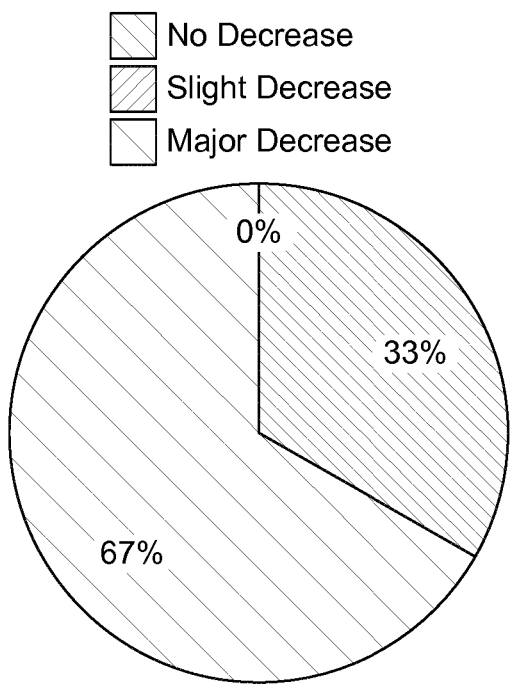
FIG. 28 illustrates a plot of effectiveness scores in reducing tremors in subjects suffering from tremors following application of AM and FM modulations in repetition in accordance with one embodiment of the present invention.

It was noted whether the patients experienced no decrease in tremors after the treatment, slight decrease in tremors, or a major decrease in tremors. The results are shown in FIG. 28.

Combined Unit

In one embodiment the apparatus comprises a plurality of applicators 103, for example, from 2 to 4 applicators 103 or from 4 to 8 applicators 103.

In one embodiment the applicators 103 can be controlled individually or in one or more groups.

This configuration allows multiple body parts to be treated simultaneously in order to shorten the overall treatment time by the number of applicators 103 used to treat each of the individual body parts at the same time with their own applicator 103. For example, it would take one hour to treat four body separate body parts for 15 minutes each with a single applicator 103, while the same treatment could be reduced to 15 minutes if four applicators 103 were employed simultaneously.

In one embodiment treatment times can further reduced after the administration of supraparamagnetic iron oxide nanoparticles (SPIONs).

In one embodiment, having a plurality of applicators 103, the frequencies of the one or more carrier signals can be offset.

In one embodiment the offset can be (i) the Fibonacci sequence, (ii) the Pythagorean tuning ratio, (iii) the Phi ratio 1.618033, and (iv) frequency tones in the ratio of the circle of fifths.

With the application of such offset, standing wave ratios consistent with chords can be delivered in order to increase efficiency and tissue stimulatory effects for the purpose of physiological stimulation, magneto hydrodynamics and mechano-transduction.

In one embodiment strong resonant standing waves created by two or more applicators 103 can be utilized to enhance the nanooscillatory dissolutions of unwanted calcifications and intracellular debris. This vibratory nanolithotripsy offers a non-invasive alternative to surgical stone removal in many parts of the body.

As discussed hereinabove, the ideal resonant frequency in the tissue can be determined as a function of shortest time of temperature rise per frequency set. Similarly, in one embodiment the ideal resonant frequency can be employed to find an optimum resonant frequency for the purpose of dissolving the stone.

Ionic Layer Activation

In one embodiment, where the modulation is in the kilohertz range, the ionic water layer outside of microtubules is targeted in order to more efficiently target cellular functions.

In other embodiments, where the modulation is in the megahertz range, the microtubules themselves are targeted in order more efficiently to target actin myosin and tubulin monomer stimulation through the efficient use of standing waves. The ability to stimulate the micro-tubular surface structure in vivo allows for the non-invasive stimulation of microtubules in vivo for use in medical applications. The energy transferred into the body by the stimulation with the or each ultra-high frequency resonant therapy applicator 103 is capable of promoting micro-tubular stability.

Disposable Applicator Pads

In one embodiment disposable, de-attachable, quick-disconnect bandage or stick-on electrolytic dielectric applicator pads for post-surgical application and therapy can be employed.

In one embodiment the or each applicator 103 is placed over a post-surgical site and adheres to the surface of the wound or area to be treated therapeutically for post-operative pain relief and wound rehabilitation.

In preferred embodiments the applicators 103 are of two formats, being (i) a dry bandage cotton surface applicator for incorporation into a bandage, and (ii) a hypoallergenic stick-on polymer gel applicator for direct site of interest application.

In one embodiment quick-disconnect radio frequency coax cables are attached to the patient bandage applicator or the hypoallergenic stick-on polymer gel applicator to the base unit radio frequency generator.

A quick-connect connector connects the temperature sensors from the applicators 103 to the base unit radio frequency generator.

Quick disconnects from the base unit to the applicators 103 allow the patient to only need to connect the cables to the applicators 103 during a therapy session and allow the patient to quickly disconnect the applicators 103 from the base unit.

In one embodiment the applicator bandage contains an EPROM memory storage in order to monitor therapy and provide a limited life use of the respective applicator 103.

In one embodiment the applicator bandage is programed to a limited number of uses in order to terminate the use of a bandage beyond its known safety ratings from a hardware prospective. In one embodiment the applicator bandage can be terminated after a certain period of time or by number of sessions for wound care and sterility.

Transcranial Magnetic Stimulation

In one embodiment the apparatus can include a skull cap, which supports one of more applicators 103, for example, one, two, three or four applicators, for the application of AM modulated UHF energy for transcranial magnetic stimulation of brain tissue in humans and animals.

In one embodiment a skull cap, optionally with Velcro® attachment, is made to receive a single patch antenna applicator 103 for AM modulated UHF application and stimulation of underlying brain tissue.

In this embodiment the single applicator 103 may be moved and positioned over the area of interest and secured in place to the skull cap.

The single applicator 103 is energized by an appropriate frequency composition over the area of interest for a user determined or machine determined time.

In another embodiment the skull cap is made to receive two patch antenna applicators 103 for AM modulated UHF application and stimulation of underlying brain tissue in stereo over opposing temporal lobes or over the frontal and occipital lobes.

The two applicators 103 are energized by an appropriate frequency composition over the area of interest for a user determined or machine determined time.

In one embodiment the double energized applicators 103 are set to apply a variety of phased intonations and harmonic vibratory compositions that allow the composition to energize and focus the UHF energy over opposing areas or targeted areas of the brain.

In one embodiment opposing applicators 103 may be set to offset frequencies in order to create a binaural signal that entrains brain signals.

In one embodiment the applicators 103 may be offset by from 0 Hz to about 35 Hz or other user-specified harmonic ratios.

The three applicators 103 are energized by an appropriate frequency composition over the area of interest for a user determined or machine determined time.

In one embodiment the triple-energized applicators 103 are set to apply a variety of phased intonations and harmonic vibratory compositions that allow the composition to energize and focus the UHF energy over opposing areas or targeted areas of the brain. Triplet harmonic tunings allow chords of vibratory energy to be tuned and focused.

The four applicators 103 are energized by an appropriate frequency composition over the area of interest for a user determined or machine determined time.

In one embodiment the quadruple energized applicators 103 are set to play a variety of phased intonations and harmonic vibratory compositions that allow the composition to energize and focus the UHF energy over single areas or group targeted areas of the brain. Quadruple harmonic tunings allow chords of vibratory energy to be tuned and focused.

In embodiments binaural stimulation in stereo and in phased array focusing is possible with the double, triple and quadruple applicator configurations.

In one embodiment chords may be created with Pythagorean tuning of base and subsequent frequencies in order to increase the resonance factor of stimulated tissues.

Pre-Conditioning Injury Prevention

The apparatus can be employed to pre-heat major muscle groups of an athlete prior to an event and cause vasodilation with accompanying oxygen delivery to tissues. Studies show that heating muscles to from 37° C. to 41° C. produces HSPs, which help form stronger tendons and ligaments and decrease sport/training related injuries, so trainers have investigated pre-warming during training for pre-conditioning.

Example

One example of a pre-conditioning composition set is as follows:
AM Modulation:
1.7 Hz
7.83 Hz
21 Hz
34 Hz
1000 Hz, each for 5 s
then repeat
In this Example, the FM modulation applies a three chord combination at the same time, as follows.
Signal 1
528 Hz continuously
Signal 2
1050 Hz continuously
Signal 3
1500 Hz continuously Post-Conditioning/Rehabilitation The apparatus can be employed to wash out lactic acid and other chemical mediators of inflammation from major tissues and allows the athlete to recover much faster, with less pain providing a better quality of life after an event—increasing blood flow, delivery of molecular oxygen to tissues, extracellular pH, lymphatic drainage, and metabolic rate (doubling approximately with each 10° C. rise in temperature).

Example

One example of a post-conditioning composition set is as follows:
AM Modulation:
1 Hz
3 Hz
108 Hz
13000 Hz
10 Hz
25000 Hz, each for 5 seconds
then repeat
In this Example, the FM modulation applies a three chord combination at the same time, as follows.
Signal 1
528 Hz continuously
Signal 2
396 Hz continuously Signal 3
852 Hz continuously
Mastitis In one embodiment the apparatus can be used to treat or prevent mastitis, such as in dairy animals or humans.

In one embodiment the apparatus can be used to deliver therapy to one or more quadrants of an udder, optionally all four quadrants, for the purpose of preventing or treating mastitis in dairy animals, like cows, sheep, goats and llamas, typically in station stalls or on a production line.

In one embodiment this therapy can be done in combination with ozonized water and antiseptic wash, which can be provided in an udder bag, which can be robotically or manually attached.

In one embodiment the udder bag can be formed or silicone.

In one embodiment the udder bag can include four or five applicators 103, with 4 applicators 103 arranged at the respective quadrants of the udder and one applicator 103 disposed below the teats facing upwards.

In one embodiment the applicators 103 are embedded in the wall of the udder bag and connected to the drive unit 105 to deliver resonant standing waves.

In one embodiment the apparatus includes temperature sensors which sense the temperature at each of the quadrants, and optionally the general environment in order to control the applicators 103 to maintain a predetermined temperature.

In one embodiment the udder bag has an udder bag irrigation assembly system which acts to disinfect and ozonize the udder while also enhancing coupling of the applicators 103 with the udder and bathing the udder in a warm, antiseptic, ozonized water bath, optionally at a temperature of from about 39° C. to 43° C.

In one embodiment the apparatus has a pretreated water reservoir, a water filtration system, a heater to pre-warm water to a temperature of from about 37° C. to about 43° C., and a computer-controlled mixer for mixing the incoming water. This temperature regulation system can also be employed to cool the udder should a temperature increase be detected.

In one embodiment the temperature of the udder bag is raised to a predetermined temperature, typically 34° C., and raised gradually over a predetermined period, typically 3 minutes, to a second, higher temperature, typically 43° C., in order not to heat shock the udder with a sudden temperature rise from a cold outside environment to 43° C. By employing water which is pre-warmed to 43° C., better and faster control of the temperature rise can be had in cold environments with the addition of the energized field of the apparatus.

In one embodiment the apparatus comprises an ozone generator, a mixing chamber for ozone and antiseptic, and a pump for filling the udder bag.

In one embodiment the apparatus further comprises a circulation pump for fluid movement in the udder bag for washing the udder washing, circulating ozonized and antiseptic fluids, discharging dirty fluids, and circulating rinsing fluids.

In one embodiment the apparatus further comprises an inline refractometer for measuring particulates and specific gravity of the wash fluid in order to maintain a clean udder state.

In one embodiment the apparatus allows for multiple washes until a specific gravity of 1.045 or less is obtained.

In one embodiment the apparatus includes an infrared sensor for determining water turbidity and quality in order to determine when an udder is clean enough to stop rinsing and to begin to recirculating clean fluid in order to conserve water.

In one embodiment the udder is pre-washed to be clean debris, and the apparatus is placed over the udder and activated. Warm Water with ozone and antiseptic is circulated and rinses the udder in a warm wash, here to remove any remaining debris, and a turbidity sensor checks to see if the udder is clean enough to begin recirculation of the antiseptic and ozonized fluids.

The temperature of the water is controlled cool to be raised over a three to five minute period in order gradually and gently to pre-heat the udder with antiseptic and ozonized fluid.

All four quadrants of the udder bag are conjointly or individually controlled by independent temperature sensors disposed over each udder and ventral teats facing upwards.

With this control, the necessary energy and frequency composition sets are selected in order to achieve and maintain a target therapeutic temperature of from about 39° C. to about 43° C. for a time period, typically from about 15 minutes to about 30 minutes.

Such pre-treatment at milking may not only decrease the incidence of mastitis in cows with reduced or minimal use of antibiotics, but also the apparatus may be pre-placed in a milking line in order to achieve not only antisepsis but also pre-warm teats and udders to enhance milk production through the increase temperature of the udder brought about by the apparatus by the warm antiseptic, ozonized fluids and radio therapy.

Example

One example of a milk parlor composition set is as follows:
AM Modulation:
Mode #1
7.82 Hz for 10 seconds
16 Hz for 10 seconds
1.25 Hz for 10 seconds
55 Hz for 10 seconds
10000 Hz for 10 seconds
444 Hz for 3 seconds
2008 Hz for 10 seconds
1.25 Hz for 10 seconds
3000 Hz for 10 seconds
16 Hz for 10 seconds
5000 Hz for 5 seconds
333 for 3 seconds
10000 Hz for 5 seconds
2720 Hz for 5 seconds
727 Hz for 5 seconds
880 Hz for 3 seconds
787 Hz for 3 seconds
393000 Hz for 3 seconds
220 Hz for 3 seconds
561930 Hz for 3 seconds
1823 Hz for 3 seconds
then repeat
Mode #2
This mode can be employed as an alternative to or in addition to the frequencies of the composition set of Mode #1.
770000 Hz for 3 seconds
770 Hz for 3 seconds 370 Hz for 3 seconds
1722 Hz for 3 seconds
then repeat In this Example, the FM modulation applies a three chord (offset) combination at the same time, as follows.

Signal 1
174 Hz for 10 seconds
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
then repeat Signal 2
285 Hz for 10 seconds
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
then repeat Signal 3
396 Hz for 10 seconds
417 Hz for 10 seconds
528 Hz for 10 seconds
639 Hz for 10 seconds
741 Hz for 10 seconds
852 Hz for 10 seconds
963 Hz for 10 seconds
174 Hz for 10 seconds
285 Hz for 10 seconds
then repeat In one embodiment the apparatus can be miniaturized with two applicators 103 and temperature sensors in a bra, fashioned for a human for the treatment of mastitis as well as oncological and other internal medicine applications where radio therapy may be of benefit.

The apparatus may be assembled with or without the ozone and antiseptic system connected to the bra as determined by the specific clinical application and specific intended procedure.

In an alternative embodiment the bra can have the applicators 103 woven into the fabric in various anatomical configurations depending on tumor site may be custom fitted into each bra to fit specific patient needs.

In one embodiment the apparatus is available as a module with the fluid system built-in as one unit.

In an alternative embodiment the fluid unit can be fluid system and the drive unit 105 can be configured as separate modules that connect to the applicators 103.

In one embodiment each bra cup can provide for antiseptic and ozonized wash may for chest wound management, in addition to the ongoing therapy as provided by the applicators 103.

In one embodiment the bra can be configured so as to be adaptable for rapid customization on the patient, whether it be a human, horse, cow or other small or exotic animal. Various sizes and shapes can be made to conform to the various shapes and sizes of the different animals.

In one embodiment a battery-operated miniaturized backpack unit can be attached to the applicator 103 so that ongoing radio therapy with or without the antiseptic and ozonized washing may be worn for extended periods, as in the treatment of antibiotic-resistant mastitis infections or bacterial, fungal and or viral origin.

In one embodiment the apparatus can be adapted for the treatment of chest wall and breast cancer with the additional circulation of nanoparticles, such as iron oxide, silver and/or gold nanoparticles, added to the antiseptic fluid, with or without the addition of ozone.

In one embodiment ultra-violet light, typically provided by LEDs, typically in the wavelength of about 434 nm to about 480 nm, can be incorporated, in spaced relation, typically at spacings of 3 cm, and super pulsed/energized in order to kill surface bacteria and fungi at the surface of the applicators 103.

Space Adaptation Syndrome

The present apparatus has application in relieving symptoms of sick astronauts suffering from the symptoms of space adaptation syndrome.

In one embodiment therapy over the auditory lobe and middle ear by an externally-applied applicators 103, typically at about 35° C., for a defined period, typically from about 10 minutes to 15 minutes, at a slow repetition rate, typically from about 1 Hz to about 3 Hz, can help relieve symptoms of vertigo and nausea caused by travel in space. In this embodiment the apparatus is used as a transcranial magnetic stimulation (TMS) device.

In one embodiment the applicators 103 can be attached to a skull-cap to position the applicators 103 around the skull.

The present apparatus acts to calm the mind and relieve nausea by application over the brainstem/base. Multiple transcranial magnetic stimulation (TMS) frequency composition sets may be used for different desired clinical outcomes.

In one embodiment the apparatus can include from to 2 to 16 applicators 103, typically, 2, 3, 4 8 or 16 applicators 103. Larger arrays of applicators 103, typically 32 or more applicators 103 can be employed with larger animals, like elephants.

The applicators 103 can be driven simultaneously in a single array, for example, as 8 to 16 applicators 103, or separate 2 or 4 arrays of applicators 103 can be applied to multiple body parts simultaneously in order to increase blood-flow, oxygenation and hsp70 production in muscle groups prone to space disuse atrophy.

In another embodiment a seat, such as a contoured chair, with a plurality of applicators 103 arranged thereon is fashioned to allow astronauts, or civilians, to sit and be rapidly warmed and resonated in order to maintain ideal muscle mass, muscle health and rehabilitation, with the ability to wash out lactic acid and other cellular mediators of inflammation and produce hsp70 in greater quantity.

Crohn's and Other Gastrointestinal Conditions

The present apparatus also has application in intravenous, intratumoral, intraperitoneal, intrathoracic injection and intestinal slurry for crones and other gastrointestinal diseases.

Deep Tissue Warming

The present apparatus also has application in enhancing the heating of deep tissues.

In one embodiment an applicator 103 can be incorporated into an item to be worn by a user, for example, a booty or mitten for warming of feet or hands.

The apparatus can be energized to bring cold hands and feet up to a warmer temperature of 35° C. to 36° C., for example, using the above-described (2T1) neurologic composition.

This warming treatment can also be used for symptom relief of diabetic neuropathy.

Finally, it will be understood that the present invention has been described in its preferred embodiments and can be modified in many different ways without departing from the scope of the invention as defined by the appended claims.

In one embodiment larger arrays of applicators 103, typically 32 or more applicators 103 can be employed with larger animals, like race horses and elephants.

In one embodiment, in systems having multiple applicators 103, fractal hierarchical management of applicator zones can be coordinated rhythmically to pulsate coordinated physiological rhythms in order to coordinate physiological processes and fluid movement through coordinated rhythmic pulsations of standing waves over body regions as determined by the clinical needs of the patient.

In one embodiment different regions may be turned on or off as needed in order to perform independent local, but globally-controlled, actions.

In one embodiment each applicator 103 can have its own artificial intelligence monitoring, which allows each applicator 103 to be maintained at a target temperature.

In one embodiment groups of applicators 103 may be controlled by a hierarchy of control and accuracy with auto-auditing feedback loops and sensor cross checks.

In one embodiment regional and individual temperature sensors can be independently and regionally monitored.

In one embodiment cooling can be achieved by artificial intelligence that turns down the power and duty cycle as needed for proper maintenance of target temperatures once achieved.

In alternative or additional embodiments water cooling can be employed by the introduction of cool water from an inflow line into the system.

The invention claimed is:

1. An apparatus for creating resonant standing waves in biological tissue, comprising a plurality of applicators for application to the biological tissue and a drive unit configured to drive the applicators simultaneously with at least one AM modulated carrier signal and a plurality of FM modulated carrier signals in order to create resonant standing waves in the tissue,
   wherein the at least one AM modulated carrier signal comprises a set of AM modulated carrier signals of a plurality of different frequencies which drive the applicators in sequence for respective periods of time, and the set of AM modulated carrier signals repeats to drive the applicators in repetitive sequence,
   wherein the FM modulated carrier signals are different from each other and applied simultaneously to drive the applicators, and
   wherein one or more of the FM modulated carrier signals comprises a set of FM modulated carrier signals of a plurality of different frequencies which drive the applicators in sequence for respective periods of time, and the set of FM modulated carrier signals repeats to drive the applicators in repetitive sequence.

2. The apparatus of claim 1, wherein the applicators are arranged in a singular array or a plurality of arrays.

3. The apparatus of claim 1, wherein three FM modulated carrier signals are applied simultaneously, as a triplet, to drive the applicators.

4. The apparatus of claim 1, wherein one or more of the carrier signals are square-wave signals.

5. The apparatus of claim 1, wherein one or more of the FM modulated carrier signals are triangular-wave signals.

6. The apparatus of claim 1, wherein one or more of the FM modulated carrier signals are sinusoidal-wave signals.

7. The apparatus of claim 1, wherein the frequency of one or more of the carrier signals is from 5 MHz to 13 MHz.

8. The apparatus of claim 1, wherein the frequency of one or more of the AM modulated carrier signals is from 100 MHz to 500 MHz.

9. The apparatus of claim 1, wherein the modulating frequency of one or more of the AM modulated carrier signals is from 2.3 GHz to 3.2 GHz.

10. The apparatus of claim 1, one or more of the AM modulated carrier signals has a center frequency of 434 MHz.

11. The apparatus of claim 1, wherein the at least one AM modulated carrier signal is modulated between a first, low-power state and a second, high-power state, thereby allowing control of power level.

12. The apparatus of claim 1, wherein the at least one AM modulated carrier signal is modulated with a frequency of from 1 Hz to 2.6 MHz.

13. The apparatus of claim 1, wherein one or more of the FM modulated carrier signals is modulated with a frequency of from 1 Hz to 50 kHz.

14. The apparatus of claim 1, wherein the at least one AM modulated carrier signal is modulated with a frequency of from 1 Hz to 1 MHz.

15. The apparatus of claim 1, wherein one or more of the FM modulated carrier signals is modulated with a frequency of from 1 Hz to 10 kHz.

16. The apparatus of claim 1, wherein one or more of the FM modulated carrier signals is modulated with a frequency of from 1 Hz to 1 kHz.

17. An apparatus for creating resonant standing waves in biological tissue, comprising a plurality of applicators for application to the biological tissue and a drive unit configured to drive the applicators simultaneously with at least one AM modulated carrier signal and a plurality of FM modulated carrier signals in order to create resonant standing waves in the tissue,
   wherein the at least one AM modulated carrier signal comprises a set of AM modulated carrier signals of a plurality of different frequencies which drive the applicators in sequence for respective periods of time, and the set of AM modulated carrier signals repeats to drive the applicators in repetitive sequence,
   wherein the FM modulated carrier signals are different from each other and applied simultaneously to drive the applicators, and all of the FM modulated carrier signals each comprise a set of FM modulated carrier signals of a plurality of different frequencies which drive the applicators in sequence for respective periods of time, and the sets of FM modulated carrier signals each repeat to drive the applicators in repetitive sequence.

18. An apparatus for creating resonant standing waves in biological tissue, comprising at least one applicator for introduction of a therapy to the biological tissue utilizing a drive unit configured to energize the at least one applicator simultaneously with at least one AM modulated carrier signal and at least one FM modulated carrier signal in order to create resonant standing waves in the biological tissue, wherein the at least one AM modulated carrier signal comprises a set of AM modulated carrier signals of a single frequency or a plurality of different frequencies and respective duty cycles which drive the at least one applicator in sequence for respective periods of time, the at least one FM modulated carrier signal comprises a set of FM modulated carrier signals of a plurality of different frequencies which drive the at least one applicator in sequence for respective periods of time, and the set of FM modulated carrier signals repeats to drive the at least one applicator in repetitive sequence.

19. The apparatus of claim 18, wherein the set of AM modulated carrier signals comprises a plurality of different frequencies, and the set of AM modulated carrier signals repeats to drive the at least one applicator in repetitive sequence.

20. The apparatus of claim 18, wherein the drive unit is configured to energize the at least one applicator with a plurality of FM modulated carrier signals, wherein the FM modulated carrier signals are different from each singular carrier and superimposed simultaneously to drive the at least one applicator.

* * * * *